(12) United States Patent
Edgerton et al.

(10) Patent No.: US 10,806,927 B2
(45) Date of Patent: *Oct. 20, 2020

(54) TRANSCUTANEOUS SPINAL CORD STIMULATION: NONINVASIVE TOOL FOR ACTIVATION OF LOCOMOTOR CIRCUITRY

(71) Applicant: The Regents of the University of California, Oakland, CA (US)

(72) Inventors: V. Reggie Edgerton, Los Angeles, CA (US); Yury Gerasimenko, Los Angeles, CA (US); Roland R. Roy, Playa Vista, CA (US); Daniel C. Lu, Rancho Palos Verdes, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/208,529

(22) Filed: Jul. 12, 2016

(65) Prior Publication Data

US 2017/0007831 A1    Jan. 12, 2017

Related U.S. Application Data

(63) Continuation of application No. 14/355,812, filed as application No. PCT/US2012/064878 on Nov. 13, 2012, now Pat. No. 9,415,218.

(Continued)

(51) Int. Cl.
*A61N 1/02* (2006.01)
*A61N 1/36* (2006.01)
(Continued)

(52) U.S. Cl.
CPC .......... *A61N 1/36034* (2017.08); *A61H 1/00* (2013.01); *A61N 1/36003* (2013.01);
(Continued)

(58) Field of Classification Search
CPC ............. A61N 1/02; A61N 1/05; A61N 1/055
(Continued)

(56) References Cited

U.S. PATENT DOCUMENTS 3,543,761 A    12/1970  Bradley
3,662,758 A    5/1972   Glover
(Continued)

FOREIGN PATENT DOCUMENTS

AU    2012204526 A1    7/2013
CA    2 823 592 A1     7/2012
(Continued)

OTHER PUBLICATIONS

U.S. Office Action dated Apr. 8, 2015 issued in U.S. Appl. No. 14/355,812.
(Continued)

*Primary Examiner* — Jon Eric C Morales
(74) *Attorney, Agent, or Firm* — Tom Hunter; Weaver Austin Villeneuve & Sampson LLP

(57) ABSTRACT

This disclosure provides non-invasive methods to induce motor control in a mammal subject to spinal cord or other neurological injuries. In certain embodiments the method involves administering transcutaneous electrical spinal cord stimulation (tSCS) to the mammal at a frequency and intensity that induces the desired locomotor activity.

15 Claims, 5 Drawing Sheets

Related U.S. Application Data

(60) Provisional application No. 61/558,892, filed on Nov. 11, 2011, provisional application No. 61/673,661, filed on Jul. 19, 2012.

(51) Int. Cl.
*A61N 1/04* (2006.01)
*A61H 1/00* (2006.01)

(52) U.S. Cl.
CPC ..... *A61N 1/36007* (2013.01); *A61N 1/36025* (2013.01); *A61H 2201/10* (2013.01)

(58) Field of Classification Search
USPC .................................. 607/3, 42, 45, 72, 74
See application file for complete search history.

(56) References Cited

U.S. PATENT DOCUMENTS

| | | | |
|---|---|---|---|
| 3,724,467 A | 4/1973 | Avery et al. |
| 4,044,774 A | 8/1977 | Corbin et al. |
| 4,102,344 A | 7/1978 | Conway et al. |
| 4,141,365 A | 2/1979 | Fischell et al. |
| 4,285,347 A | 8/1981 | Hess |
| 4,340,063 A | 7/1982 | Maurer |
| 4,379,462 A | 4/1983 | Borkan et al. |
| 4,414,986 A | 11/1983 | Dickhudt et al. |
| 4,538,624 A | 9/1985 | Tarjan |
| 4,549,556 A | 10/1985 | Tajan et al. |
| 4,559,948 A | 12/1985 | Liss et al. |
| 4,800,898 A | 1/1989 | Hess et al. |
| 4,934,368 A | 6/1990 | Lynch |
| 4,969,452 A | 11/1990 | Petrofsky et al. |
| 5,002,053 A | 3/1991 | Garcia-Rill et al. |
| 5,031,618 A | 7/1991 | Mullett |
| 5,066,272 A | 11/1991 | Eaton et al. |
| 5,081,989 A | 1/1992 | Graupe et al. |
| 5,121,754 A | 6/1992 | Mullett |
| 5,344,439 A | 9/1994 | Often |
| 5,354,320 A | 10/1994 | Schaldach et al. |
| 5,374,285 A | 12/1994 | Vaiani et al. |
| 5,417,719 A | 5/1995 | Hull et al. |
| 5,476,441 A | 12/1995 | Durfee et al. |
| 5,562,718 A | 10/1996 | Palermo |
| 5,643,330 A | 7/1997 | Holsheimer et al. |
| 5,733,322 A | 3/1998 | Starkebaum |
| 5,983,141 A | 11/1999 | Sluijter et al. |
| 6,066,163 A | 5/2000 | John |
| 6,104,957 A | 8/2000 | Alo et al. |
| 6,122,548 A | 9/2000 | Starkebaum et al. |
| 6,308,103 B1 | 10/2001 | Gielen |
| 6,319,241 B1 | 11/2001 | King et al. |
| 6,470,213 B1 | 10/2002 | Alley |
| 6,500,110 B1 | 12/2002 | Davey et al. |
| 6,503,231 B1 | 1/2003 | Prausnitz et al. |
| 6,505,074 B2 | 1/2003 | Boveja et al. |
| 6,551,849 B1 | 4/2003 | Kenney |
| 6,587,724 B2 | 7/2003 | Mann |
| 6,662,053 B2 | 12/2003 | Borkan |
| 6,666,831 B1 | 12/2003 | Edgerton et al. |
| 6,685,729 B2 | 2/2004 | Gonzalez |
| 6,819,956 B2 | 11/2004 | DiLorenzo |
| 6,839,594 B2 | 1/2005 | Cohen et al. |
| 6,871,099 B1 | 3/2005 | Whitehurst et al. |
| 6,892,098 B2 | 5/2005 | Ayal et al. |
| 6,895,280 B2 | 5/2005 | Meadows et al. |
| 6,895,283 B2 | 5/2005 | Erickson et al. |
| 6,937,891 B2 | 8/2005 | Leinders et al. |
| 6,950,706 B2 | 9/2005 | Rodriguez et al. |
| 6,975,907 B2 | 12/2005 | Zanakis et al. |
| 6,988,006 B2 | 1/2006 | King et al. |
| 6,999,820 B2 | 2/2006 | Jordan |
| 7,020,521 B1 | 3/2006 | Brewer et al. |
| 7,024,247 B2 | 4/2006 | Gliner et al. |
| 7,035,690 B2 | 4/2006 | Goetz |
| 7,047,084 B2 | 5/2006 | Erickson et al. |
| 7,065,408 B2 | 6/2006 | Herman et al. |
| 7,096,070 B1 | 8/2006 | Jenkins et al. |
| 7,110,820 B2 | 9/2006 | Tcheng et al. |
| 7,127,287 B2 | 10/2006 | Duncan et al. |
| 7,127,296 B2 | 10/2006 | Bradley |
| 7,127,297 B2 | 10/2006 | Law et al. |
| 7,153,242 B2 | 12/2006 | Goffer |
| 7,184,837 B2 | 2/2007 | Goetz |
| 7,200,443 B2 | 4/2007 | Faul |
| 7,209,787 B2 | 4/2007 | DiLorenzo |
| 7,228,179 B2 | 6/2007 | Campen et al. |
| 7,239,920 B1 | 7/2007 | Thacker et al. |
| 7,251,529 B2 | 7/2007 | Greenwood-Van Meerveld |
| 7,252,090 B2 | 8/2007 | Goetz |
| 7,313,440 B2 | 12/2007 | Miesel et al. |
| 7,324,853 B2 | 1/2008 | Ayal et al. |
| 7,330,760 B2 | 2/2008 | Heruth et al. |
| 7,337,005 B2 | 2/2008 | Kim et al. |
| 7,337,006 B2 | 2/2008 | Kim et al. |
| 7,381,192 B2 | 6/2008 | Brodard et al. |
| 7,415,309 B2 | 8/2008 | Mcintyre |
| 7,463,928 B2 | 12/2008 | Lee et al. |
| 7,467,016 B2 | 12/2008 | Colborn |
| 7,493,170 B1 | 2/2009 | Segel et al. |
| 7,496,404 B2 | 2/2009 | Meadows et al. |
| 7,502,652 B2 | 3/2009 | Gaunt et al. |
| 7,536,226 B2 | 5/2009 | Williams et al. |
| 7,544,185 B2 | 6/2009 | Bengtsson |
| 7,584,000 B2 | 9/2009 | Erickson |
| 7,590,454 B2 | 9/2009 | Garabedian et al. |
| 7,603,178 B2 | 10/2009 | North et al. |
| 7,628,750 B2 | 12/2009 | Cohen et al. |
| 7,660,636 B2 | 2/2010 | Castel et al. |
| 7,697,995 B2 | 4/2010 | Cross et al. |
| 7,729,781 B2 | 6/2010 | Swoyer et al. |
| 7,734,340 B2 | 6/2010 | De Ridder |
| 7,734,351 B2 | 6/2010 | Testerman et al. |
| 7,769,463 B2 | 8/2010 | Katsnelson |
| 7,797,057 B2 | 9/2010 | Harris |
| 7,801,601 B2 | 9/2010 | Maschino et al. |
| 7,813,803 B2 | 10/2010 | Heruth et al. |
| 7,813,809 B2 | 10/2010 | Strother et al. |
| 7,856,264 B2 * | 12/2010 | Firlik ............... A61M 5/14276 607/3 |
| 7,877,146 B2 | 1/2011 | Rezai et al. |
| 7,890,182 B2 | 2/2011 | Parramon |
| 7,949,395 B2 | 5/2011 | Kuzma |
| 7,949,403 B2 | 5/2011 | Palermo et al. |
| 7,987,000 B2 | 7/2011 | Moffitt et al. |
| 7,991,465 B2 | 8/2011 | Bartic et al. |
| 8,019,427 B2 | 9/2011 | Moffitt |
| 8,050,773 B2 | 11/2011 | Zhu |
| 8,108,052 B2 | 1/2012 | Boling |
| 8,131,358 B2 | 3/2012 | Moffitt et al. |
| 8,155,750 B2 | 4/2012 | Jaax et al. |
| 8,170,660 B2 | 5/2012 | Dacey, Jr. et al. |
| 8,190,262 B2 | 5/2012 | Gerber et al. |
| 8,195,304 B2 | 6/2012 | Strother et al. |
| 8,214,048 B1 | 7/2012 | Whitehurst et al. |
| 8,229,565 B2 | 7/2012 | Kim et al. |
| 8,239,038 B2 | 8/2012 | Wolf, II |
| 8,260,436 B2 | 9/2012 | Gerber et al. |
| 8,271,099 B1 | 9/2012 | Swanson |
| 8,295,936 B2 | 10/2012 | Wahlstrand et al. |
| 8,311,644 B2 | 11/2012 | Moffitt et al. |
| 8,332,029 B2 | 12/2012 | Glukhovsky et al. |
| 8,346,366 B2 | 1/2013 | Arle et al. |
| 8,352,036 B2 | 1/2013 | DiMarco et al. |
| 8,355,791 B2 | 1/2013 | Moffitt |
| 8,355,797 B2 | 1/2013 | Caparso et al. |
| 8,364,273 B2 | 1/2013 | De Ridder |
| 8,369,961 B2 | 2/2013 | Christman et al. |
| 8,412,345 B2 | 4/2013 | Moffitt |
| 8,428,728 B2 | 4/2013 | Sachs |
| 8,442,655 B2 | 5/2013 | Moffitt et al. |
| 8,452,406 B2 | 5/2013 | Arcot-Krishnamurthy et al. |
| 8,588,884 B2 | 11/2013 | Hegde et al. |
| 8,700,145 B2 | 4/2014 | Kilgard et al. |

(56) References Cited

U.S. PATENT DOCUMENTS

| | | |
|---|---|---|
| 8,712,546 B2 | 4/2014 | Kim et al. |
| 8,750,957 B2 | 6/2014 | Tang et al. |
| 8,805,542 B2 | 8/2014 | Tai et al. |
| 9,072,891 B1 | 7/2015 | Rao |
| 9,101,769 B2 | 8/2015 | Edgerton et al. |
| 9,205,259 B2 | 12/2015 | Kim et al. |
| 9,205,260 B2 | 12/2015 | Kim et al. |
| 9,205,261 B2 | 12/2015 | Kim et al. |
| 9,272,143 B2 | 3/2016 | Libbus et al. |
| 9,283,391 B2 | 3/2016 | Ahmed |
| 9,393,409 B2 | 7/2016 | Edgerton et al. |
| 9,415,218 B2 | 8/2016 | Edgerton et al. |
| 9,610,442 B2 | 4/2017 | Yoo et al. |
| 9,993,642 B2 * | 6/2018 | Gerasimenko ..... A61N 1/36003 |
| 10,137,299 B2 | 11/2018 | Lu et al. |
| 2002/0055779 A1 | 5/2002 | Andrews |
| 2002/0111661 A1 | 8/2002 | Cross et al. |
| 2002/0115945 A1 | 8/2002 | Herman et al. |
| 2002/0193843 A1 | 12/2002 | Hill et al. |
| 2003/0032992 A1 | 2/2003 | Thacker et al. |
| 2003/0078633 A1 | 4/2003 | Firlik et al. |
| 2003/0100933 A1 | 5/2003 | Ayal et al. |
| 2003/0158583 A1 | 8/2003 | Burnett et al. |
| 2003/0220679 A1 | 11/2003 | Han |
| 2003/0233137 A1 | 12/2003 | Paul, Jr. |
| 2004/0039425 A1 | 2/2004 | Greenwood-Van Meerveld |
| 2004/0044380 A1 | 3/2004 | Bruninga et al. |
| 2004/0111118 A1 | 6/2004 | Hill et al. |
| 2004/0111126 A1 | 6/2004 | Tanagho et al. |
| 2004/0122483 A1 | 6/2004 | Nathan et al. |
| 2004/0127954 A1 | 7/2004 | McDonald et al. |
| 2004/0133248 A1 | 7/2004 | Frei et al. |
| 2004/0138518 A1 | 7/2004 | Rise et al. |
| 2005/0004622 A1 | 1/2005 | Cullen et al. |
| 2005/0070982 A1 | 3/2005 | Heruth et al. |
| 2005/0075669 A1 | 4/2005 | King |
| 2005/0075678 A1* | 4/2005 | Faul ..... A61N 1/36007 607/41 |
| 2005/0102007 A1 | 5/2005 | Ayal et al. |
| 2005/0113882 A1 | 5/2005 | Cameron et al. |
| 2005/0119713 A1 | 6/2005 | Whitehurst et al. |
| 2005/0125045 A1 | 6/2005 | Brighton et al. |
| 2005/0209655 A1 | 9/2005 | Bradley et al. |
| 2005/0246004 A1 | 11/2005 | Cameron et al. |
| 2005/0278000 A1 | 12/2005 | Strother et al. |
| 2006/0003090 A1 | 1/2006 | Rodger et al. |
| 2006/0041295 A1 | 2/2006 | Osypka |
| 2006/0089696 A1 | 4/2006 | Olsen et al. |
| 2006/0100671 A1 | 5/2006 | Ridder |
| 2006/0111754 A1 | 5/2006 | Rezai et al. |
| 2006/0122678 A1 | 6/2006 | Olsen et al. |
| 2006/0142816 A1 | 6/2006 | Fruitman et al. |
| 2006/0142822 A1 | 6/2006 | Tulgar |
| 2006/0149333 A1 | 7/2006 | Tanagho et al. |
| 2006/0149337 A1 | 7/2006 | John |
| 2006/0239482 A1 | 10/2006 | Hatoum |
| 2007/0016097 A1 | 1/2007 | Farquhar et al. |
| 2007/0016266 A1 | 1/2007 | Paul, Jr. |
| 2007/0049814 A1 | 3/2007 | Muccio |
| 2007/0055337 A1 | 3/2007 | Tanrisever |
| 2007/0060954 A1 | 3/2007 | Cameron et al. |
| 2007/0060980 A1 | 3/2007 | Strother et al. |
| 2007/0073357 A1 | 3/2007 | Rooney et al. |
| 2007/0083240 A1 | 4/2007 | Peterson et al. |
| 2007/0156179 A1 | 7/2007 | S.E. |
| 2007/0168008 A1 | 7/2007 | Olsen |
| 2007/0179534 A1 | 8/2007 | Firlik et al. |
| 2007/0191709 A1 | 8/2007 | Swanson |
| 2007/0208381 A1 | 9/2007 | Hill et al. |
| 2007/0233204 A1 | 10/2007 | Lima et al. |
| 2007/0255372 A1 | 11/2007 | Metzler et al. |
| 2007/0265679 A1 | 11/2007 | Bradley et al. |
| 2007/0265691 A1 | 11/2007 | Swanson |
| 2007/0276449 A1 | 11/2007 | Gunter et al. |
| 2007/0276450 A1 | 11/2007 | Meadows et al. |
| 2008/0021513 A1 | 1/2008 | Thacker et al. |
| 2008/0046049 A1 | 2/2008 | Skubitz et al. |
| 2008/0051851 A1* | 2/2008 | Lin ..... A61N 1/05 607/42 |
| 2008/0071325 A1 | 3/2008 | Bradley |
| 2008/0103579 A1 | 5/2008 | Gerber |
| 2008/0140152 A1 | 6/2008 | Imran et al. |
| 2008/0140169 A1 | 6/2008 | Imran |
| 2008/0147143 A1 | 6/2008 | Popovic et al. |
| 2008/0154329 A1 | 6/2008 | Pyles et al. |
| 2008/0183224 A1 | 7/2008 | Barolat |
| 2008/0200749 A1 | 8/2008 | Zheng et al. |
| 2008/0207985 A1 | 8/2008 | Farone |
| 2008/0215113 A1 | 9/2008 | Pawlowicz |
| 2008/0221653 A1 | 9/2008 | Agrawal et al. |
| 2008/0228241 A1 | 9/2008 | Sachs |
| 2008/0228250 A1 | 9/2008 | Mironer |
| 2008/0234791 A1 | 9/2008 | Arle et al. |
| 2008/0279896 A1 | 11/2008 | Heinen et al. |
| 2009/0012436 A1 | 1/2009 | Lanfermann et al. |
| 2009/0093854 A1 | 4/2009 | Leung et al. |
| 2009/0112281 A1 | 4/2009 | Miyazawa et al. |
| 2009/0118365 A1 | 5/2009 | Benson, III et al. |
| 2009/0157141 A1 | 6/2009 | Chiao et al. |
| 2009/0198305 A1 | 8/2009 | Naroditsky et al. |
| 2009/0204173 A1 | 8/2009 | Fang et al. |
| 2009/0270960 A1 | 10/2009 | Zhao et al. |
| 2009/0281599 A1 | 11/2009 | Thacker et al. |
| 2009/0299166 A1 | 12/2009 | Nishida et al. |
| 2009/0299167 A1 | 12/2009 | Seymour |
| 2009/0306491 A1 | 12/2009 | Haggers |
| 2010/0004715 A1 | 1/2010 | Fahey |
| 2010/0023103 A1 | 1/2010 | Elborno |
| 2010/0042193 A1 | 2/2010 | Slavin |
| 2010/0070007 A1 | 3/2010 | Parker et al. |
| 2010/0114239 A1 | 5/2010 | McDonald et al. |
| 2010/0125313 A1 | 5/2010 | Lee et al. |
| 2010/0137938 A1 | 6/2010 | Kishawi et al. |
| 2010/0145428 A1 | 6/2010 | Cameron et al. |
| 2010/0152811 A1 | 6/2010 | Flaherty |
| 2010/0185253 A1 | 7/2010 | Dimarco et al. |
| 2010/0198298 A1 | 8/2010 | Glukhovsky et al. |
| 2010/0217355 A1 | 8/2010 | Tass et al. |
| 2010/0241191 A1 | 9/2010 | Testerman et al. |
| 2010/0268299 A1 | 10/2010 | Farone |
| 2010/0274312 A1 | 10/2010 | Alataris et al. |
| 2010/0305660 A1 | 12/2010 | Hegi et al. |
| 2010/0318168 A1 | 12/2010 | Bighetti |
| 2010/0331925 A1 | 12/2010 | Peterson |
| 2011/0029040 A1 | 2/2011 | Walker et al. |
| 2011/0040349 A1 | 2/2011 | Graupe |
| 2011/0054567 A1 | 3/2011 | Lane et al. |
| 2011/0054568 A1 | 3/2011 | Lane et al. |
| 2011/0054579 A1 | 3/2011 | Kumar et al. |
| 2011/0125203 A1 | 5/2011 | Simon et al. |
| 2011/0130804 A1 | 6/2011 | Lin et al. |
| 2011/0152967 A1 | 6/2011 | Simon et al. |
| 2011/0160810 A1 | 6/2011 | Griffith |
| 2011/0166546 A1 | 7/2011 | Jaax et al. |
| 2011/0184488 A1 | 7/2011 | De Ridder |
| 2011/0184489 A1 | 7/2011 | Nicolelis et al. |
| 2011/0218594 A1 | 9/2011 | Doran et al. |
| 2011/0224665 A1 | 9/2011 | Crosby et al. |
| 2011/0224752 A1 | 9/2011 | Rolston et al. |
| 2011/0224753 A1 | 9/2011 | Palermo et al. |
| 2011/0224757 A1 | 9/2011 | Zdeblick et al. |
| 2011/0230701 A1 | 9/2011 | Simon et al. |
| 2011/0245734 A1 | 10/2011 | Wagner et al. |
| 2011/0276107 A1 | 11/2011 | Simon et al. |
| 2011/0288609 A1 | 11/2011 | Tehrani et al. |
| 2011/0295100 A1 | 12/2011 | Rolston et al. |
| 2012/0006793 A1 | 1/2012 | Swanson |
| 2012/0029528 A1 | 2/2012 | Macdonald et al. |
| 2012/0035684 A1 | 2/2012 | Thompson et al. |
| 2012/0101326 A1 | 4/2012 | Simon et al. |
| 2012/0109251 A1 | 5/2012 | Lebedev et al. |
| 2012/0109295 A1 | 5/2012 | Fan |
| 2012/0123293 A1 | 5/2012 | Shah et al. |
| 2012/0126392 A1 | 5/2012 | Kalvesten et al. |

(56) References Cited

U.S. PATENT DOCUMENTS

| | | |
|---|---|---|
| 2012/0165899 A1 | 6/2012 | Gliner |
| 2012/0172946 A1 | 7/2012 | Altaris et al. |
| 2012/0179222 A1 | 7/2012 | Jaax et al. |
| 2012/0185020 A1* | 7/2012 | Simon .............. A61N 2/006 607/74 |
| 2012/0197338 A1 | 8/2012 | Su et al. |
| 2012/0221073 A1 | 8/2012 | Southwell et al. |
| 2012/0232615 A1 | 9/2012 | Barolat et al. |
| 2012/0252874 A1 | 10/2012 | Feinstein et al. |
| 2012/0259380 A1 | 10/2012 | Pyles |
| 2012/0277824 A1 | 11/2012 | Li |
| 2012/0277834 A1 | 11/2012 | Mercanzini et al. |
| 2012/0283697 A1 | 11/2012 | Kim et al. |
| 2012/0283797 A1 | 11/2012 | De Ridder |
| 2012/0302821 A1 | 11/2012 | Burnett |
| 2012/0310305 A1 | 12/2012 | Kaula et al. |
| 2012/0310315 A1 | 12/2012 | Savage et al. |
| 2012/0330391 A1 | 12/2012 | Bradley et al. |
| 2013/0013041 A1 | 1/2013 | Glukhovsky et al. |
| 2013/0030319 A1 | 1/2013 | Hettrick et al. |
| 2013/0030501 A1 | 1/2013 | Feler et al. |
| 2013/0053734 A1 | 2/2013 | Barriskill et al. |
| 2013/0066392 A1 | 3/2013 | Simon et al. |
| 2013/0085317 A1 | 4/2013 | Feinstein |
| 2013/0110196 A1 | 5/2013 | Alataris et al. |
| 2013/0123568 A1 | 5/2013 | Hamilton et al. |
| 2013/0123659 A1 | 5/2013 | Bartol et al. |
| 2013/0165991 A1 | 6/2013 | Kim et al. |
| 2013/0197408 A1 | 8/2013 | Goldfarb et al. |
| 2013/0253299 A1 | 9/2013 | Weber et al. |
| 2013/0253611 A1 | 9/2013 | Lee et al. |
| 2013/0268016 A1 | 10/2013 | Xi et al. |
| 2013/0268021 A1 | 10/2013 | Moffitt |
| 2013/0281890 A1 | 10/2013 | Mishelevich |
| 2013/0289446 A1 | 10/2013 | Stone et al. |
| 2013/0303873 A1 | 11/2013 | Voros et al. |
| 2013/0304159 A1 | 11/2013 | Simon et al. |
| 2013/0310911 A1 | 11/2013 | Tai et al. |
| 2014/0031893 A1 | 1/2014 | Walker et al. |
| 2014/0046407 A1 | 2/2014 | Ben-Ezra et al. |
| 2014/0058490 A1 | 2/2014 | DiMarco |
| 2014/0066950 A1 | 3/2014 | Macdonald et al. |
| 2014/0067007 A1 | 3/2014 | Drees et al. |
| 2014/0067354 A1 | 3/2014 | Kaula et al. |
| 2014/0081071 A1 | 3/2014 | Simon et al. |
| 2014/0100633 A1 | 4/2014 | Mann et al. |
| 2014/0107397 A1 | 4/2014 | Simon et al. |
| 2014/0107398 A1 | 4/2014 | Simon et al. |
| 2014/0114374 A1 | 4/2014 | Rooney et al. |
| 2014/0163640 A1 | 6/2014 | Edgerton et al. |
| 2014/0180361 A1 | 6/2014 | Burdick et al. |
| 2014/0213842 A1 | 7/2014 | Simon et al. |
| 2014/0236257 A1 | 8/2014 | Parker et al. |
| 2014/0296752 A1 | 10/2014 | Edgerton et al. |
| 2014/0303901 A1 | 10/2014 | Sadeh |
| 2014/0316484 A1 | 10/2014 | Edgerton et al. |
| 2014/0316503 A1 | 10/2014 | Tai et al. |
| 2014/0324118 A1 | 10/2014 | Simon et al. |
| 2014/0330067 A1 | 11/2014 | Jordan |
| 2014/0330335 A1 | 11/2014 | Errico et al. |
| 2014/0357936 A1 | 12/2014 | Simon et al. |
| 2015/0065559 A1 | 3/2015 | Feinstein et al. |
| 2015/0165226 A1 | 6/2015 | Simon et al. |
| 2015/0182784 A1 | 7/2015 | Barriskill et al. |
| 2015/0190634 A1 | 7/2015 | Rezai et al. |
| 2015/0231396 A1 | 8/2015 | Burdick et al. |
| 2015/0265830 A1 | 9/2015 | Simon et al. |
| 2016/0030737 A1 | 2/2016 | Gerasimenko et al. |
| 2016/0030748 A1 | 2/2016 | Edgerton et al. |
| 2016/0045727 A1 | 2/2016 | Rezai et al. |
| 2016/0045731 A1 | 2/2016 | Simon et al. |
| 2016/0074663 A1 | 3/2016 | De Ridder |
| 2016/0121109 A1 | 5/2016 | Edgerton et al. |
| 2016/0121114 A1 | 5/2016 | Simon et al. |
| 2016/0121116 A1 | 5/2016 | Simon et al. |
| 2016/0175586 A1 | 6/2016 | Edgerton et al. |
| 2016/0220813 A1 | 8/2016 | Edgerton et al. |
| 2016/0235977 A1 | 8/2016 | Lu et al. |
| 2016/0339239 A1 | 11/2016 | Yoo et al. |
| 2017/0157389 A1 | 6/2017 | Tai et al. |
| 2017/0165497 A1 | 6/2017 | Lu |
| 2017/0246450 A1 | 8/2017 | Liu et al. |
| 2017/0246452 A1 | 8/2017 | Liu et al. |
| 2017/0274209 A1 | 9/2017 | Edgerton et al. |
| 2017/0296837 A1 | 10/2017 | Jin |
| 2018/0185642 A1 | 7/2018 | Lu |
| 2018/0256906 A1 | 9/2018 | Pivonka et al. |
| 2018/0280693 A1 | 10/2018 | Edgerton et al. |
| 2018/0361146 A1 | 12/2018 | Gerasimenko et al. |
| 2019/0022371 A1 | 1/2019 | Chang et al. |
| 2019/0167987 A1 | 6/2019 | Lu et al. |
| 2019/0381313 A1 | 12/2019 | Lu |

FOREIGN PATENT DOCUMENTS

| | | |
|---|---|---|
| EP | 2661307 A2 | 11/2013 |
| EP | 2968940 A1 | 1/2016 |
| RU | 2130326 C1 | 5/1999 |
| RU | 2141851 C1 | 11/1999 |
| RU | 2160127 C1 | 12/2000 |
| RU | 2178319 C2 | 1/2002 |
| RU | 2192897 C2 | 11/2002 |
| RU | 2001102533 | 11/2002 |
| RU | 2226114 C1 | 3/2004 |
| RU | 2258496 C2 | 8/2005 |
| RU | 2361631 C2 | 7/2009 |
| RU | 2368401 C1 | 9/2009 |
| RU | 2387467 C1 | 4/2010 |
| RU | 2396995 C2 | 8/2010 |
| RU | 2397788 C2 | 8/2010 |
| RU | 2445990 C1 | 3/2012 |
| RU | 2471518 C2 | 1/2013 |
| RU | 2475283 C2 | 2/2013 |
| WO | WO 97/047357 A1 | 12/1997 |
| WO | WO 03/026735 A2 | 4/2003 |
| WO | WO 03/092795 A1 | 11/2003 |
| WO | WO 2004/087116 A2 | 10/2004 |
| WO | WO 2005/051306 A2 | 6/2005 |
| WO | WO 2005/087307 A2 | 9/2005 |
| WO | WO 2007/007058 A1 | 1/2007 |
| WO | WO 2007/107831 A2 | 9/2007 |
| WO | WO 2008/109862 A1 | 9/2008 |
| WO | WO 2008/121891 A1 | 10/2008 |
| WO | WO 2009/042217 A1 | 4/2009 |
| WO | WO 2009/111142 A2 | 9/2009 |
| WO | WO 2010/055421 A1 | 5/2010 |
| WO | WO 2010/114998 A1 | 10/2010 |
| WO | WO 2010/124128 A1 | 10/2010 |
| WO | WO 2012/094346 A2 | 7/2012 |
| WO | WO 2012/100260 A2 | 7/2012 |
| WO | WO 2012/129574 A2 | 9/2012 |
| WO | WO 2013/071307 A1 | 5/2013 |
| WO | WO 2013/071309 A1 | 5/2013 |
| WO | WO 2014/144785 A1 | 9/2014 |
| WO | WO 2015/048563 A2 | 4/2015 |
| WO | WO 2016/029159 A2 | 2/2016 |
| WO | WO 2016/033369 A1 | 3/2016 |
| WO | WO 2016/033372 A1 | 3/2016 |
| WO | WO 2017/011410 A1 | 1/2017 |
| WO | WO 2017/024276 A1 | 2/2017 |
| WO | WO 2017/035512 A1 | 3/2017 |
| WO | WO 2017/044904 A1 | 3/2017 |
| WO | WO 2018/140531 A1 | 8/2018 |
| WO | WO 2018/217791 A1 | 11/2018 |
| WO | WO 2020/041502 A1 | 2/2020 |
| WO | WO 2020/041633 A1 | 2/2020 |

OTHER PUBLICATIONS

U.S. Final Office Action dated Sep. 21, 2015 issued in U.S. Appl. No. 14/355,812.

U.S. Notice of Allowance dated Apr. 13, 2016 issued in U.S. Appl. No. 14/355,812.

(56) References Cited

OTHER PUBLICATIONS

U.S. Office Action dated Jul. 13, 2016 issued in U.S. Appl. No. 14/775,618.
PCT International Search Report dated Jul. 30, 2012 issued in PCT/US2012/020112.
PCT International Preliminary Report on Patentability and Written Opinion dated Jul. 10, 2013 issued in PCT/US2012/020112.
PCT International Search Report and Written Opinion dated Mar. 19, 2013 issued in PCT/US2012/064878.
PCT International Preliminary Report on Patentability dated May 22, 2014 issued in PCT/US2012/064878.
Australian Patent Examination Report No. 1 dated Jul. 11, 2016 issued in AU 2012334926.
European Communication pursuant to Rule 114(2) EPC regarding observations by a third party dated Mar. 27, 2015 issued in EP 12 847 885.6.
European Extended Search Report dated May 6, 2015 issued in EP 12 847 885.6.
European Office Action dated Apr. 15, 2016 issued in EP 12 847 885.6.
European Reply to Communication of Apr. 15, 2016 dated Oct. 24, 2016 in EP 12 847 885.6.
European Second Office Action dated Feb. 16, 2017 issued in EP 12 847 885.6.
PCT Declaration of Non-Establishment of International Search Report and Written Opinion dated Dec. 24, 2014 issued in PCT/US2014/057886.
PCT International Preliminary Report on Patentability and Written Opinion dated Apr. 7, 2016 issued in PCT/US2014/057886.
PCT International Search Report and Written Opinion dated Aug. 6, 2014 issued in PCT/US2014/029340.
PCT International Preliminary Report on Patentability dated Sep. 24, 2015 issued in PCT/US2014/029340.
European Extended Search Report dated Nov. 8, 2016 issued in EP 14 76 5477.6.
PCT International Search Report and Written Opinion dated Dec. 5, 2016 issued in PCT/US2016/045898.
PCT International Search Report and Written Opinion dated Dec. 8, 2015 issued in PCT/US2015/047268.
PCT International Preliminary Report on Patentability and Written Opinion dated Feb. 28, 2017 issued in PCT/US2015/047268.
PCT International Search Report and Written Opinion dated Dec. 3, 2015 issued in PCT/US2015/047272.
PCT International Preliminary Report on Patentability and Written Opinion dated Feb. 28, 2017 issued in PCT/US2015/047272.
PCT Declaration of Non-Establishment of International Search Report and Written Opinion dated Dec. 1, 2015 issued in PCT/US2015/046378.
PCT International Preliminary Report on Patentability and Written Opinion dated Feb. 21, 2017 issued in PCT/US2015/046378.
PCT International Search Report and Written Opinion dated Dec. 5, 2016 issued in PCT/US2016/049129.
PCT International Search Report dated Mar. 19, 2013 issued in PCT/US2012/064874.
PCT International Search Report dated Mar. 19, 2013 issued in PCT/US2012/064878.
PCT International Search Report dated Sep. 3, 2012 issued in PCT/US2012/022257.
PCT International Search Report dated Oct. 31, 2012 issued in PCT/US2012/030624.
Angeli et al. (2014) "Altering spinal cord excitability enables voluntary movements after chronic complete paralysis in humans" *Brain* 137: 1394-1409.
Courtine, Grégoire et al. (2007) "Modulation of multisegmental monosynaptic responses in a variety of leg muscles during walking and miming in humans," *J Physiol.* 582.3:1125-1139.
Danner S.M., Hofstoetter U.S., Ladenbauer J., Rattay F., and Minassian K. (Mar. 2011) "Can the human lumbar posterior columns be stimulated by transcutaneous spinal cord stimulation? A modeling study" *Europe PMC Funders Author Manuscripts, Artif Organs* 35(3):257-262, 12 pp.
DeSantana et al. (Dec. 2008) "Effectiveness of Transcutaneous Electrical Nerve Stimulation for Treatment of Hyperalgesia and Pain," *Curr Rheumatol Rep.* 10(6):492-499, 12 pp.
Dubinsky, Richard M. and Miyasaki, Janis, "Assessment: Efficacy of transcutaneous electric nerve stimulation in the treatment of pain in neurologic disorders (an evidence-based review)," Report of the Therapeutics and Technology Assessment Subcommittee of the American Academy of Neurology, (2010) *Neurology*, 74:173-176.
Fong et al. (2009) "Recovery of control of posture and locomotion after a spinal cord injury: solutions staring us in the face," *Progress in Brain Research*, Elsevier Amsterdam, NL,175:393-418.
Ganley et al., (2005) "Epidural Spinal Cord Stimulation Improves Locomoter Performance in Low ASIA C, Wheelchair-Dependent, Spinal Cord-Injured Individuals: Insights from Metabolic Response," *Top. Spinal Cord Inj. Rehabil*;11(2):50-63.
Gerasimenko Y., Gorodnichev R., Machueva E., Pivovarova E., Semyenov D., Savochin A., Roy R.R., and Edgerton V.R., (Mar. 10, 2010) "Novel and Direct Access to the Human Locomotor Spinal Circuitry," *J Neurosci.* 30(10):3700-3708, PMC2847395.
Gerasimenko Y.P., Ichiyama R.M., Lavrov I.A., Courtine G., Cai L., Zhong H., Roy R.R., and Edgerton V.R. (2007) "Epidural Spinal Cord Stimulation Plus Quipazine Administration Enable Stepping in Complete Spinal Adult Rats," *J Neurophysiol*. 98:2525-2536.
Harkema et al. (2011) "Effect of Epidural stimulation of the lumbosacral spinal cord on voluntary movement, standing, and assisted stepping after motor complete paraplegia: a case study" *Lancet* 377(9781): 1938-1947; NIH Public Access Author Manuscript 17 pages [doi:10.1016/S0140-6736(11)60547-3].
Herman R., He J., D'Luzansky S., Willis W., Dilli S., (2002) "Spinal cord stimulation facilitates functional walking in a chronic, incomplete spinal cord injured," *Spinal Cord*. 40:65-68.
Hofstoetter, U.S. et al. (Aug. 2008) "Modification of Reflex Responses to Lumbar Posterior Root Stimulation by Motor Tasks in Healthy Subjects," *Artif Organs*, 32(8):644-648.
Ichiyama et al. (2005) "Hindlimb stepping movements in complete spinal rats induced by epidural spinal cord stimulation" *Neuroscience Letters*, 383:339-344.
Kitano K., Koceja D.M. (2009) "Spinal reflex in human lower leg muscles evoked by transcutaneous spinal cord stimulation," *J Neurosci Methods*. 180:111-115.
Minasian et al. (2010) "Transcutaneous stimulation of the human lumbar spinal cord: Facilitating locomotor output in spinal cord injury," *Conf. Proceedings Soc. for Neurosci.*, Abstract No. 286.19, 1 page.
Minassian et al. (Aug. 2011) "Transcutaneous spinal cord stimulation," *International Society for Restorative Neurology*, http://restorativeneurology.org/resource-center/assessments/transcutaneous-lumbar-spinal-cord-stimulation/;http://restorativeneurology.org/wp-content/uploads/2011/08/Transcutaneous-spinal-cord-stimulation_long.pdf, 6 pp.
Minassian et al. (Mar. 2007) "Posterior root-muscle reflexes elicited by transcutaneous stimulation of the human lumbosacral cord," *Muscle & Nerve* 35:327-336.
Nandra et al., (2014) "Microelectrode Implants for Spinal Cord Stimulation in Rats," *Thesis, California Institute of Technology*, Pasadena, California, Defended on Sep. 24, 2014, 104 pages.
Nandra et al., (Jan. 23, 2011) "A Parylene-Based Microelectrode Arrary Implant for Spinal Cord Stimulation in Rats," *Conf. Proc. IEEE Eng. Med. Biol. Soc.*, pp. 1007-1010.
Rodger et al., (2007) "High Density Flexible Parylene-Based Multielectrode Arrays for Retinal and Spinal Cord Stimulation," Transducers & Eurosensors, Proc. of the 14th International Conference on Solid-State Sensors, Actuators and Microsystems, Lyon, France, Jun. 10-14, 2007, IEEE, pp. 1385-1388.
Seifert et al. (Nov. 1, 2002) "Restoration of Movement Using Functional Electrical Stimulation and Bayes' Theorem," *The Journal of Neuroscience*, 22(1):9465-9474.

(56) References Cited

OTHER PUBLICATIONS

Tanabe et al. (2008) "Effects of transcutaneous electrical stimulation combined with locomotion-like movement in the treatment of post-stroke gait disorder: a single-case study," 30(5):411-416 abstract, 1 page.
Ward, Alex R. (Feb. 2009) "Electrical Stimulation Using Kilohertz-Frequency Alternating Current," (2009) *Phys Ther*.89(2):181-190 [published online Dec. 18, 2008].
U.S. Office Action dated Oct. 3, 2017 issued in U.S. Appl. No. 15/025,201.
U.S. Final Office Action dated Apr. 25, 2017 issued in U.S. Appl. No. 14/775,618.
U.S. Notice of Allowance dated Jan. 18, 2018 issued in U.S. Appl. No. 14/775,618.
European Extended Search Report dated May 10, 2017 issued in EP 14849355.4.
Australian Patent Examination Report No. 1 dated May 11, 2018 issued in AU 2014228794.
PCT International Preliminary Report on Patentability and Written Opinion dated Feb. 15, 2018 issued in PCT/US2016/045898.
European Extended Search Report dated Mar. 1, 2018 issued in EP 15836927.2.
European Extended Search Report dated Apr. 4, 2018 issued in EP 15834593.4.
PCT International Search Report and Written Opinion dated Sep. 12, 2016 issued in PCT/US2016/041802.
PCT International Preliminary Report on Patentability and Written Opinion dated Jan. 25, 2018 issued in PCT/US2016/041802.
PCT International Preliminary Report on Patentability and Written Opinion dated Mar. 8, 2018 issued in PCT/US2016/049129.
U.S. Notice of Allowance dated Aug. 1, 2018 issued in U.S. Appl. No. 15/025,201.
Canadian Office Action dated Aug. 31, 2018 issued in CA 2,864,473.
Australian Examination report No. 1 dated Jan. 11, 2019 issued in AU 2014324660.
European Office Action dated Jul. 20, 2018 issued in EP 14849355.4.
European Office Action dated Nov. 14, 2018 issued in EP 14 76 5477.6.
European Extended Search Report dated Dec. 13, 2018 issued in EP 16833973.7.
PCT International Search Report and Written Opinion dated Mar. 12, 2018 issued in PCT/US2018/015098.
PCT International Search Report and Written Opinion dated Aug. 31, 2018 issued in PCT/US2018/033942.
U.S. Office Action dated Jul. 22, 2019 issued in U.S. Appl. No. 15/506,696.
U.S. Office Action dated Jun. 4, 2019 issued in U.S. Appl. No. 15/505,053.
U.S. Office Action dated Apr. 17, 2019 issued in U.S. Appl. No. 15/344,381.
Canadian Office Action dated Jul. 30, 2019 issued in CA 2,864,473.
European Office Action dated Sep. 27, 2019 issued in EP 14765477.6.
Australian Patent Examination Report No. 1 dated Jul. 18, 2019 issued in AU 2015308779.
Australian Patent Examination Report No. 1 dated Jun. 14, 2019 issued in AU 2015305237.
European Office Action dated Jul. 17, 2019 issued in EP 15834593.4.
European Extended Search Report dated Feb. 19, 2019 issued in EP 16825005.8.
PCT International Preliminary Report on Patentability and Written Opinion dated Jul. 30, 2019 issued in PCT/US2018/015098.
Andersson, et al., (2003) "CNS Involvement in Overactive Bladder." *Drugs*, 63(23): 2595-2611.
Edgerton and Harkema (2011) "Epidural stimulation of the spinal cord in spinal cord injury: current status and future challenges" *Expert Rev Neurother*. 11(10): 1351-1353. doi:10.1586/ern.11.129 [NIH Public Access—Author Manuscript—5 pages].
U.S. Office Action dated Jan. 8, 2020 issued in U.S. Appl. No. 15/975,678.
U.S. Office Action dated Oct. 31, 2019 issued in U.S. Appl. No. 15/750,499.
U.S. Notice of Allowance dated Feb. 13, 2020 issued in U.S. Appl. No. 15/505,053.
U.S. Final Office Action dated Dec. 30, 2019 issued in U.S. Appl. No. 15/344,381.
Australian Examination report No. 2 dated Nov. 7, 2019 issued in AU 2014324660.
Australian Examination report No. 3 dated Jan. 6, 2020 issued in AU 2014324660.
Australian Patent Examination Report No. 1 dated Jan. 6, 2020 issued in AU 2019206059.
PCT International Preliminary Report on Patentability and Written Opinion dated Nov. 26, 2019 issued in PCT/US2018/033942.
PCT International Search Report and Written Opinion dated Nov. 14, 2019 issued in PCT/US2019/047777.
PCT International Search Report and Written Opinion dated Nov. 21, 2019 issued in PCT/US2019/047551.
Kapetanakis, et al. (2017) "Cauda Equina Syndrome Due to Lumbar Disc Herniation: a Review of Literature," *Folia Medial*, 59(4): 377-86.
Wang, et al. (2017) "Incidence of C5 nerve root palsy after cervical surgery," *Medicine*, 96(45), 14 pages.

\* cited by examiner

TRANSCUTANEOUS SPINAL CORD STIMULATION: NONINVASIVE TOOL FOR ACTIVATION OF LOCOMOTOR CIRCUITRY

CROSS-REFERENCE TO RELATED APPLICATIONS

This application is a continuation of U.S. application Ser. No. 14/355,812 filed May 1, 2014, which is a U.S. 371 National Phase of PCT/US2012/064878, filed on Nov. 13, 2012, which claims the benefit of U.S. Provisional Application No. 61/558,892 filed Nov. 11, 2011, and U.S. Provisional Application No. 61/673,661 filed Jul. 19, 2012, both of which are incorporated by reference in their entirety. Additionally, U.S. patent application Ser. Nos. 13/342,903, 13/356,499, and 13/430,557 are incorporated by reference in their entirety.

STATEMENT OF GOVERNMENTAL SUPPORT

This invention was made with Government support under NS062009, awarded by the National Institutes of Health. The Government has certain rights in the invention.

BACKGROUND

Field of the Disclosure

The present disclosure relates to the field of neurological treatment and rehabilitation for injury and disease including traumatic spinal cord injury, non-traumatic spinal cord injury, stroke, movement disorders, brain injury, ALS, Neurodegenerative Disorder, Dementia, Parkinson's disease, and other diseases or injuries that result in paralysis and/or nervous system disorder. Devices, pharmacological agents, and methods are provided to facilitate recovery of posture, locomotion, and voluntary movements of the arms, trunk, and legs, and recovery of autonomic, sexual, vasomotor, speech, swallowing, and respiration, in a human subject having spinal cord injury, brain injury, or any other neurological disorder.

Description of the Related Art

Serious spinal cord injuries (SCI) affect approximately 1.3 million people in the United States, and roughly 12-15, 000 new injuries occur each year. Of these injuries, approximately 50% are complete spinal cord injuries in which there is essentially total loss of sensory motor function below the level of the spinal lesion.

Neuronal networks formed by the interneurons of the spinal cord that are located in the cervical and lumbar enlargements, such as the spinal networks (SNs), play an important role in the control of posture, locomotion and movements of the upper limbs, breathing and speech. Most researchers believe that all mammals, including humans, have SNs in the lumbosacral cord. See Dimitrijevic, M. R, Gerasimenko, Yu., and Pinter, M. M., Evidence for a Spinal Central Pattern Generator in Humans, Ann. N. Y. Acad. Sci., 1998, vol. 860, p. 360; Gurfinkel', V. S., Levik, Yu. S., Kazennikov, O. V., and Selionov, V. A., Does the Prime Mover of Stepping Movements Exist in Humans?, *Human Physiology*, 1998, vol. 24, no. 3, p. 42; Gerasimenko, Yu. P., Roy, R. R., and Edgerton, V R., Epidural Stimulation: Comparison of the Spinal Circuits That Generate and Control Locomotion in Rats, Cats and Humans, *Exp. Neurol.*, 2008, vol. 209, p. 417. Normally, the activity of SNs is regulated supraspinally and by peripheral sensory input. In the case of disorders of the connections between the brain and spinal cord, e.g., as a result of traumatic spinal cord lesions, motor tasks can be enabled by epidural electrical stimulation of the lumbosacral and cervical segments as well as the brainstem. It has been shown that epidural electrical spinal cord stimulation (eESCS) with sufficient intensity can induce electromyographic (EMG) patterns in the leg muscles of patients with clinically complete spinal cord injury. See Dimitrijevic, Gerasimenko, Yu., and Pinter, supra; Minassian, K., Persy, I., Rattay, F, Pinter, M. M., Kern, H., and Dimitrijevic, M. R., Human Lumbar Cord Circuitries Can Be Activated by Extrinsic Tonic Input to Generate Locomotor-Like Activity, *Human 1Hovement Sci.*, 2007, vol. 26, p. 275; Harkema, S., Gerasimenko, Y, Hodes, J., Burdick, J., Angeli, e., Chen, Y, Ferreira, e., Willhite, A., Rejc, E., Grossman, R. G., and Edgerton, V R., Epidural Stimulation of the Lumbosacral Spinal Cord Enables Voluntary Movement, Standing, and Assisted Stepping in a Paraplegic Human, *Lancet*, 2011, vol. 377, p. 1938. eESCS is an invasive method and requires surgical implantation of electrodes on the dorsal surface of the spinal cord, which limits this method of activating SNs to clinics.

Recently, noninvasive methods for activating the SNs by means of leg muscle vibration and spinal cord electromagnetic stimulation was suggested. It was found that the vibration of the tendons of the hip muscles initiates involuntary walking movements in subjects lying on their side with an external support for the legs. See Gurfinkel', VS., Levik, Yu. S., Kazennikov, O. V, and Selionov, V A., Locomotor-Like Movements Evoked by Leg Muscle Vibration in Humans, *Eur. J lVeurosci.*, 1998, vol. 10, p. 1608; Selionov, V A., Ivanenko, Yu. P., Solopova, 1A., and Gurfinkel', VS., Tonic Central and Sensory Stimuli Facilitate Involuntary Air-Stepping in Humans, *J Neurophysiol.*, 2009, vol. 101, p. 2847. In addition, electromagnetic stimulation of the rostral segments of the lumbar spinal cord caused involuntary walking movements in healthy subjects in a similar position with a support for the legs. See Gerasimenko, Yu., Gorodnichev, R., Machueva, E., Pivovarova, E., Semenov, D., Savochin, A., Roy, R. R., and Edgerton, V R., Novel and Direct Access to the Human Locomotor Spinal Circuitry, *J New'osci.*, 2010, vol. 30, p. 3700; Gorodnichev, R. M., Machueva, E. M., Pivovarova, E. A., Semenov, D. V, Ivanov, S. M., Savokhin, A. A., Edgerton, V R., and Gerasimenko, Yu. P., A New Method for the Activation of the Locomotor Circuitry in Humans, *Hum. Physiol.*, 2010, vol. 36, no. 6, p. 700. Step-like movements elicited by vibration and electromagnetic stimulation, have apparently a different origin. In the former case, the SN is activated by afferent input mainly due to the activation of muscle receptors, whereas in the latter case, the neuronal locomotor network is affected directly. Each of these methods has its specificity. For example, the vibratory muscle stimulation elicits involuntary locomotor movements only in the hip and knee joints, without the involvement of the ankle. In addition, these characteristic movements could be evoked only in 50% of the subjects. See Selionov, Ivanenko, Solopova, and Gurfinkel', supra. The percentage of subjects in whom the spinal cord electromagnetic stimulation evoked involuntary step like movements was even smaller (10%), although in this case, the kinematic structure of the resultant movements was consistent with the natural random step-like movements to a greater extent than in the case of vibration. See Gerasimenko, Gorodnichev, Machueva, Pivovarova, Semenov, Savochin, Roy, and Edgerton, supra; Gorodnichev, Machueva, Pivovarova, Semenov, Ivanov, Savokhin, Edgerton, and Gerasimenko, supra. In addition, spinal cord electromagnetic stimulation is limited by the technical capabilities of the stimulator. The modem magnetic stimulator used in clinics (e.g., Magstim Rapid) can provide only short-exposure stimulating effects. The electromagnetic stimulator, with the parameters required to elicit step-like movements (5 Hz and 1.5 T), could be sustained for only 15 s.

SUMMARY

Embodiments of the disclosure are for use with a mammal including a human who has a spinal cord with at least one selected dysfunctional spinal circuit or other neurologically derived source of control of movement in a portion of the subject's body. It has been shown that transcutaneous electrical spinal cord stimulation (tESCS) applied in the region of the T11-T12 vertebrae with a frequency of 5-40 Hz elicited involuntary step-like movements in healthy subjects with their legs suspended in a gravity-neutral position. The amplitude of evoked step-like movements increased with increasing tESCS frequency. The frequency of evoked step-like movements did not depend on the frequency of tESCS. It was shown that the hip, knee, and ankle joints were involved in the evoked movements. In conclusion, transcutaneous electrical spinal cord stimulation (tESCS) can be used as a noninvasive method in rehabilitation of spinal pathology. By way of non-limiting examples, application of transcutaneous electrical spinal cord stimulation (tESCS) activates spinal locomotor networks (SNs), in part via the dorsal roots and the gray matter of the spinal cord. When activated, the SNs may (a) enable voluntary movement of muscles involved in at least one of standing, stepping, reaching, grasping, voluntarily changing positions of one or both legs, breathing, speech control, voiding the patient's bladder, voiding the patient's bowel, postural activity, and locomotor activity; (b) enable or improve autonomic control of at least one of cardiovascular function, body temperature, and metabolic processes; and/or (c) help facilitate recovery of at least one of an autonomic function, sexual function, or vasomotor function. According to some embodiments, the present disclosure provides that the spinal circuitry is neuromodulated to a physiological state that facilitates or enables the recovery or improved control of movement following some neuromotor dysfunction.

The paralysis may be a motor complete paralysis or a motor incomplete paralysis. The paralysis may have been caused by a spinal cord injury classified as motor complete or motor incomplete. The paralysis may have been caused by an ischemic or traumatic brain injury. The paralysis may have been caused by an ischemic brain injury that resulted from a stroke or acute trauma. By way of another example, the paralysis may have been caused by a neurodegenerative condition affecting the brain and/or spinal cord. The neurodegenerative brain injury may be associated with at least one of Parkinson's disease, Huntington's disease, Alzheimer's, Frontotemporal Dementia, dystonia, ischemic, stroke, amyotrophic lateral sclerosis (ALS), primary lateral sclerosis (PLS), and other conditions such as cerebral palsy and Multiple Sclerosis.

By way of non-limiting example, a method includes applying electrical stimulation to a portion of a spinal cord or brainstem of the subject. The electrical stimulation may be applied by a surface electrode(s) that is applied to the skin surface of the subject. Such an electrode may be positioned at, at least one of a thoracic region, a cervical region, a lumbosacral region of the spinal cord and/or the brainstem. The electrical stimulation is delivered at 5-40 Hz at 20-100 mA. While not a requirement, the electrical stimulation may not directly activate muscle cells in the portion of the patient's body having the paralysis. The electrical stimulation may include at least one of tonic stimulation and intermittent stimulation. The electrical stimulation may include simultaneous or sequential stimulation of different regions of the spinal cord.

If the paralysis was caused by a spinal cord injury at a first location along the spinal cord, the electrical stimulation may be applied by an electrode that is on the spinal cord of the patient at a second location below the first location along the spinal cord relative to the patient's brain.

Optionally, the method may include administering one or more neuropharmaceutical agents to the patient. The neuropharmaceutical agents may include at least one of a serotonergic drug, a dopaminergic drug, a noradrenergic drug, a GABAergic drug, and glycinergic drugs. By way of non-limiting examples, the neuropharmaceutical agents may include at least one of 8-OHDPAT, Way 100.635, Quipazine, Ketanserin, SR. 57227A, Ondanesetron, SB 269970, Buspirone, Methoxamine, Prazosin, Clonidine, Yohimbine, SKF-81297, SCH-23390, Quinpirole, and Eticlopride.

The electrical stimulation is defined by a set of parameter values, and activation of the selected spinal circuit may generate a quantifiable result. Optionally, the method may be repeated using electrical stimulation having different sets of parameter values to obtain quantifiable results generated by each repetition of the method. Then, a machine learning method may be executed by at least one computing device. The machine learning method builds a model of a relationship between the electrical stimulation applied to the spinal cord and the quantifiable results generated by activation of the at least one spinal circuit. A new set of parameters may be selected based on the model. By way of a non-limiting example, the machine learning method may implement a Gaussian Process Optimization.

Another exemplary embodiment is a method of enabling one or more functions selected from a group consisting of postural and/or locomotor activity, voluntary movement of leg position when not bearing weight, improved breathing and ventilation, speech control, swallowing, voluntary voiding of the bladder and/or bowel, return of sexual function, autonomic control of cardiovascular function, body temperature control, and normalized metabolic processes, in a human subject having a neurologically derived paralysis. The method includes stimulating the spinal cord of the subject using a surface electrode while subjecting the subject to physical training that exposes the subject to relevant postural proprioceptive signals, locomotor proprioceptive signals, and supraspinal signals. At least one of the stimulation and physical training modulates in real time provoke or incite the electrophysiological properties of spinal circuits in the subject so the spinal circuits are activated by at least one of supraspinal information and proprioceptive information derived from the region of the subject where the selected one or more functions are facilitated.

The region where the selected one or more functions are facilitated may include one or more regions of the spinal cord that control (a) lower limbs; (b) upper limbs and brainstem for controlling speech; (c) the subject's bladder; (d) the subject's bowel and/or other end organ. The physical training may include standing, stepping, sitting down, laying down, reaching, grasping, stabilizing sitting posture, and/or stabilizing standing posture.

The surface electrode may include an array of one or more electrodes stimulated in a monopolar biphasic configuration. Such a surface electrode may be placed over at least one of a lumbosacral portion of the spinal cord, a thoracic portion of the spinal cord, a cervical portion of the spinal cord and/or the brainstem.

The stimulation may include tonic stimulation and/or intermittent stimulation. The stimulation may include simultaneous or sequential stimulation, or combinations thereof, of different spinal cord regions. Optionally, the stimulation pattern may be under control of the subject.

The physical training may include inducing a load bearing positional change in the region of the subject where locomotor activity is to be facilitated. The load bearing positional change in the subject may include standing, stepping, reaching, and/or grasping. The physical training may include robotically guided training.

The method may also include administering one or more neuropharmaceuticals. The neuropharmaceuticals may include at least one of a serotonergic drug, a dopaminergic drug, a noradrenergic drug, a GABAergic drug, and a glycinergic drug.

Another exemplary embodiment is a method that includes placing an electrode on the patient's spinal cord, positioning the patient in a training device configured to assist with physical training that is configured to induce neurological signals in the portion of the patient's body having the paralysis, and applying electrical stimulation to a portion of a spinal cord of the patient, such as a biphasic signal of 30-40 Hz at 85-100 mA.

Another exemplary embodiment is a system that includes a training device configured to assist with physically training of the patient, a surface electrode array configured to be applied on the patient's spinal cord, and a stimulation generator connected to the electrode. When undertaken, the physical training induces neurological signals in the portion of the patient's body having the paralysis. The stimulation generator is configured to apply electrical stimulation to the electrode. Electrophysiological properties of at least one spinal circuit in the patient's spinal cord is modulated by the electrical stimulation and at least one of (1) a first portion of the induced neurological signals and (2) supraspinal signals such that the at least one spinal circuit is at least partially activatable by at least one of (a) the supraspinal signals and (b) a second portion of the induced neurological signals.

BRIEF DESCRIPTION OF THE DRAWINGS

FIG. 2A: Subject R: the cinematogramms of the joint movements of the right leg and the EMGs of the hip muscles of the right and left legs are shown. Under the EMG, there is a mark of the stimulus. At the right of the cinematogram and EMGs, there are vertical marks of the amplitude in angle degrees and mV, respectively. The duration of records is 40 s. FIG. 2B: Subject S: the EMGs of the hip and ankle muscles of the right leg and the goniograms of the knee joints of the right and left legs; the arrows at the top show the beginning and end of stimulation; the horizontal and vertical labels next to EMG, 10 s and 0.5 mV, respectively; the vertical mark to the right of the goniograms, 200 m V. H, hip; Kn, knee; Ank, ankle; RF, m. rectus femoris; BF, m. biceps femoris; T A, m. tibialis anterior; M G, m. gastrocnemius; (r), on the right; (1), on the left.

DETAILED DESCRIPTION

Figure 1:
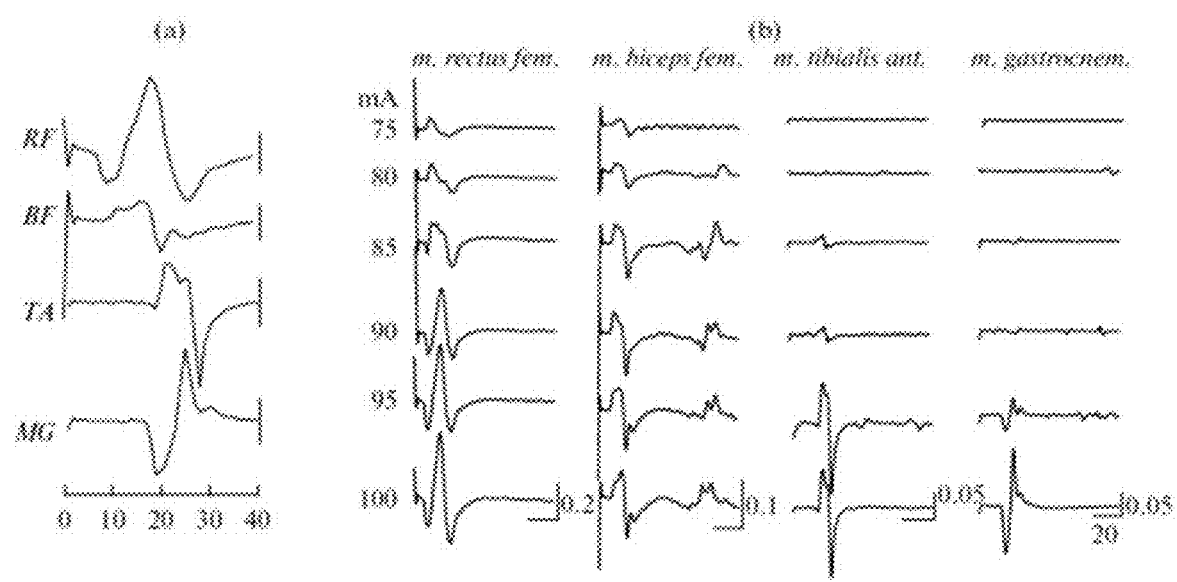
FIG. 1, panels a and b, show motor responses in the muscles of the right leg to the tESCS with a frequency of 1 Hz and an amplitude of 75-100 mA (showed at the left of the recordings). The responses in the m. rectus femoris and m. biceps femoris (RF and BF, respectively), as well as in the m. tibialis anterior and m. gastrocnemius (TA and MG, respectively) are shown. At the right bottom of the lower recording, there are marks of time in ms, the same for all the muscles, and marks of the amplitude in mV.

Unless defined otherwise, technical and scientific terms used herein have the same meaning as commonly understood by one of ordinary skill in the art to which this disclosure belongs.

The term "motor complete" when used with respect to a spinal cord injury indicates that there is no motor function below the lesion, (e.g., no movement can be voluntarily induced in muscles innervated by spinal segments below the spinal lesion.

The term "monopolar stimulation" refers to stimulation between a local electrode and a common distant return electrode.

The term "autonomic function" refers to functions controlled by the peripheral nervous system that are controlled largely below the level of consciousness, and typically involve visceral functions. Illustrative autonomic functions include, but are not limited to control of bowel, bladder, and body temperature.

The term "sexual function" refers to the ability to sustain a penile erection, have an orgasm (male or female), generate viable sperm, and/or undergo an observable physiological change associated with sexual arousal.

It was discovered that transcutaneous electrical stimulation (TCS) of the spinal cord can induce activation locomotor circuitry in a mammal (e.g., in a human or a non-human mammal). It was demonstrated, for example, that continuous tSCS at 5-40 Hz applied paraspinally over T11-T12 vertebrae at 40-70 mA induced involuntary locomotor like stepping movements in subjects with their legs in a gravity-independent position. The increase of frequency of tSCS from 5 to 30 Hz resulted in augmentation of the amplitude of evoked stepping movements. In chronic spinal cats (3 weeks after spinal cord transection at Th8) tSCS at L5 (a frequency of 5 Hz and intensity ranged from 3 to 10 mA) evoked EMG stepping pattern in hindlimb muscles in all (N=4) of tested animals, while locomotor-like movements produced by tSCS were not weight-bearing.

By non-limiting example, transcutaneous electrical stimulation can be applied to facilitate restoration of locomotion and other neurologic function in subjects suffering with spinal cord injury, as well as other neurological injury and illness. Successful application can provide a device for widespread use in rehabilitation of neurologic injury and disease.

In various embodiments, methods, devices, and optional pharmacological agents are provided to facilitate movement in a mammalian subject (e.g., a human) having a spinal cord injury, brain injury, or other neurological disease or injury. In certain embodiments, the methods involve stimulating the spinal cord of the subject using a surface electrode where the stimulation modulates the electrophysiological properties of selected spinal circuits in the subject so they can be activated by proprioceptive derived information and/or input from supraspinal. In various embodiments, the stimulation is typically accompanied by physical training (e.g., movement) of the region where the sensory-motor circuits of the spinal cord are located.

In particular illustrative embodiments, the devices, optional pharmacological agents, and methods described herein stimulate the spinal cord with, e.g., electrodes that modulate the proprioceptive and supraspinal information which controls the lower limbs during standing and/or stepping and/or the upper limbs during reaching and/or grasping conditions. It is the proprioceptive and cutaneous sensory information that guides the activation of the muscles in a coordinated manner and in a manner that accommodates the external conditions, e.g., the amount of loading, speed, and direction of stepping or whether the load is equally dispersed on the two lower limbs, indicating a standing event, alternating loading indicating stepping, or sensing postural adjustments signifying the intent to reach and grasp.

Unlike approaches that involve specific stimulation of motor neurons to directly induce a movement, the methods described herein enable the spinal circuitry to control the movements. More specifically, the devices, optional pharmacological agents, and methods described herein exploit the spinal circuitry and its ability to interpret proprioceptive information and to respond to that proprioceptive information in a functional way. In various embodiments, this is in contrast to other approaches where the actual movement is induced/controlled by direct stimulation (e.g., of particular motor neurons).

In one illustrative embodiment, the subject is fitted with one or more surface electrodes that afford selective stimulation and control capability to select sites, mode(s), and intensity of stimulation via electrodes placed superficially over, for example, the lumbosacral spinal cord and/or cervical spinal cord to facilitate movement of the arms and/or legs of individuals with a severely debilitating neuromotor disorder.

The subject is provided the generator control unit and is fitted with an electrode(s) and then tested to identify the most effective subject specific stimulation paradigms for facilitation of movement (e.g., stepping and standing and/or arm and/or hand movement). Using these stimulation paradigms, the subject practices standing, stepping, reaching, grabbing, breathing, and/or speech therapy in an interactive rehabilitation program while being subject to spinal stimulation.

Depending on the site/type of injury and the locomotor activity it is desired to facilitate, particular spinal stimulation protocols include, but are not limited to, specific stimulation sites along the lumbosacral, thoracic, and/or cervical spinal cord; specific combinations of stimulation sites along the lumbosacral, thoracic, and/or cervical spinal cord; specific stimulation amplitudes; specific stimulation polarities (e.g., monopolar and bipolar stimulation modalities); specific stimulation frequencies; and/or specific stimulation pulse widths.

In various embodiments, the system is designed so that the patient can use and control it in the home environment.

In various embodiments, the approach is not to electrically induce a walking pattern or standing pattern of activation, but to enable/facilitate it so that when the subject manipulates their body position, the spinal cord can receive proprioceptive information from the legs (or arms) that can be readily recognized by the spinal circuitry. Then, the spinal cord knows whether to step or to stand or to do nothing. In other words, this enables the subject to begin stepping or to stand or to reach and grasp when they choose after the stimulation pattern has been initiated.

Moreover, the methods and devices described herein are effective in a spinal cord injured subject that is clinically classified as motor complete; that is, there is no motor function below the lesion. In various embodiments, the specific combination of electrode(s) activated/stimulated and/or the desired stimulation of any one or more electrodes and/or the stimulation amplitude (strength) can be varied in real time, e.g., by the subject. Closed loop control can be embedded in the process by engaging the spinal circuitry as a source of feedback and feedforward processing of proprioceptive input and by voluntarily imposing fine tuning modulation in stimulation parameters based on visual, and/or kinetic, and/or kinematic input from selected body segments.

In various embodiments, the devices, optional pharmacological agents, and methods are designed so that a subject with no voluntary movement capacity can execute effective standing and/or stepping and/or reaching and/or grasping. In addition, the approach described herein can play an important role in facilitating recovery of individuals with severe although not complete injuries.

The approach described herein can provide some basic postural, locomotor and reaching and grasping patterns on their own. However, they are also likely to be a building block for future recovery strategies. Based on certain successes in animals and some preliminary human studies (see below), it appears that a strategy combining effective transcutaneous stimulation of the appropriate spinal circuits with physical rehabilitation and pharmacological intervention can provide practical therapies for complete SCI human patients. There is sufficient evidence from our work that such an approach should be enough to enable weight bearing standing, stepping and/or reaching or grasping. Such capability can give SCI patients with complete paralysis or other neuromotor dysfunctions the ability to participate in exercise, which is known to be highly beneficial for their physical and mental health. We also expect our method should enable movement with the aid of assistive walkers. While far from complete recovery of all movements, even simple standing and short duration walking would increase these patients autonomy and quality of life. The stimulating array technology described herein (e.g., transcutaneous electrical stimulation) paves the way for a direct brain-to-spinal cord interface that could enable more lengthy and finer control of movements.

While the methods and devices described herein are discussed with reference to complete spinal injury, it will be recognized that they can apply to subjects with partial spinal injury, subjects with brain injuries (e.g., ischemia, traumatic brain injury, stroke, and the like), and/or subjects with neurodegenerative diseases (e.g., Parkinson's disease, Alzheimer's disease, Huntington's disease, amyotrophic lateral sclerosis (ALS), primary lateral sclerosis (PLS), cerebral palsy, and the like).

In various embodiments, the methods combine the use of transcutaneous stimulating electrode(s) with physical training (e.g., rigorously monitored (robotic) physical training), optionally in combination with pharmacological techniques. The methods enable the spinal cord circuitry to utilize sensory input as well as newly established functional connections from the brain to circuits below the spinal lesion as a source of control signals. The approach is thus designed to enable and facilitate the natural sensory input as well as supraspinal connections to the spinal cord in order to control movements, rather than induce the spinal cord to directly induce the movement. That is, we facilitate and enhance the intrinsic neural control mechanisms of the spinal cord that exist post-SCI, rather than replace or ignore them.

Processing of Sensory Input by the Lumbosacral Spinal Cord: Using Afferents as a Source of Control In various embodiments the methods and devices described herein exploit spinal control of locomotor activity. For example, the human spinal cord can receive sensory input associated with a movement such as stepping, and this sensory information can be used to modulate the motor output to accommodate the appropriate speed of stepping and level of load that is imposed on lower limbs. Moreover, we have demonstrated that the human lumbosacral spinal cord has central-pattern-generation-like properties. Thus, oscillations of the lower limbs can be induced simply by vibrating the vastus lateralis muscle of the lower limb, by transcutaneous stimulation, and by stretching the hip. The methods described herein exploit the fact that the human spinal cord, in complete or incomplete SCI subjects, can receive and interpret proprioceptive and somatosensory information that can be used to control the patterns of neuromuscular activity among the motor pools necessary to generate particular movements, e.g., standing, stepping, reaching, grasping, and the like. The methods described herein facilitate and adapt the operation of the existing spinal circuitry that generates, for example, cyclic step-like movements via a combined approach of transcutaneous stimulation, physical training, and, optionally, pharmacology.

Facilitating Stepping and Standing in Humans Following a Clinically Complete Lesion Locomotion in mammals is attributed to intrinsic oscillating spinal neural networks capable of central pattern generation interacting with sensory information (Edgerton et al., *J. American Paraplegia Soc*, 14(4) (1991), 150-157; Forssberg, *J. Neurophysiol*, 42(4): 936-953 (1979); Grillner and Wallen, *Annu. Rev. Neurosci.*, 8: 233-261 (1985); Grillner and Zangger, *Exp Brain Res*, 34(2): 241-261 (1979)). These networks play critical roles in generating the timing of the complex postural and rhythmic motor patterns executed by motor neurons.

As indicated above, the methods described herein can involve stimulation of one or more regions of the spinal cord in combination with locomotory activities. It was our discovery that spinal stimulation in combination with locomotor activity results in the modulation of the electrophysiological properties of spinal circuits in the subject so they are activated by Proprioceptive information derived from the region of the subject where locomotor activity is to be facilitated. Further, we also determined that spinal stimulation in combination with pharmacological agents and locomotor activity results in the modulation of the electrophysiological properties of spinal circuits in the subject so they are activated by proprioceptive information derived from the region of the subject where locomotor activity is to be facilitated.

Locomotor activity of the region of interest can be accomplished by any of a number of methods known, for example, to physical therapists. By way of illustration, individuals after severe SCI can generate standing and stepping patterns when provided with body weight support on a treadmill and manual assistance. During both stand and step training of human subjects with SCI, the subjects can be placed on a treadmill in an upright position and suspended in a harness at the maximum load at which knee buckling and trunk collapse can be avoided. Trainers positioned, for example, behind the subject and at each leg assist as needed in maintaining proper limb kinematics and kinetics appropriate for each specific task. During bilateral standing, both legs can be loaded simultaneously and extension can be the predominant muscular activation pattern, although co-activation of flexors can also occur. Additionally, or alternatively, during stepping the legs are loaded in an alternating pattern and extensor and flexor activation patterns within each limb also alternated as the legs moved from stance through swing. Afferent input related to loading and stepping rate can influence these patterns, and training has been shown to improve these patterns and function in clinically complete SCI subjects.

Transcutaneous Stimulation of the Lumbosacral Spinal Cord

As indicated above, without being bound by a particular theory, it is believed that transcutaneous stimulation, e.g., over the throacic spinal cord in combination with physical training can facilitate recovery of stepping and standing in human subjects following a complete SCI.

Spinal cord electrical stimulation has been successfully used in humans for suppression of pain and spasticity (see, e.g., Johnson and Burchiel, *Neurosurgery*, 55(1): 135-141 (2004); discussion 141-142; Shealy et al., *AnesthAnalg*, 46(4): 489-491 (1967); Campos et al., *Appl. Neurophysiol.* 50(1-6): 453-454 (1987); Dimitrijevic and Sherwood, *Neurology*, 30 (7 Pt 2): 19-27 (1980); Barolat *Arch. Med. Res.*, 31(3): 258-262 (2000); Barolat, *J. Am. Paraplegia Soc.*, 11(1): 9-13 (1988); Richardson et al., *Neurosurgery*, 5(3): 344-348). Recent efforts to optimize stimulation parameters have led to a number of research studies focusing on the benefits of transcutaneous spinal cord stimulation. We have demonstrated that the location of the electrode and its stimulation parameters are important in defining the motor response. Use of surface electrode(s), as described herein, facilitates selection or alteration of particular stimulation sites as well as the application of a wide variety of stimulation parameters.

The following non-limiting examples are offered for illustrative purposes.

Example 1

Transcutaneous Electrical Stimulation of the Spinal Cord: A Noninvasive Tool for the Activation of Stepping Pattern Generators in Humans A noninvasive method for activating the SN by means of transcutaneous electrical spinal cord stimulation (tESCS) is demonstrated in this Example. The method is based on our research that showed that a single dermal electric stimulus applied in the region of the T11-T 12 vertebrae caused monosynaptic reflexes in the proximal and distal leg muscles in healthy subjects (see Courtine, G., Harkema S. J, Dy, C. J., Gerasimenko, Yu. P., and Dyhre-Poulsen, P., Modulation of Multisegmental Monosynaptic Responses in a Variety of Leg Muscles during Walking and Running in Humans, *J Physiology,* 2007, vol. 585, p. 1125) and in patients with clinically complete (ASIA A) spinal cord injury. See Dy, C. J., Gerasimenko, YP., Edgerton, V R., DyhrePoulsen P., Courtine G., Harkema S., Phase-Dependent Modulation of Percutaneously Elicited Multisegmental Muscle Responses after Spinal Cord Injury, *J Neurophysiol.,* 2010, vol. 103, p. 2808. Taking into consideration that eESCS affects the SN through mono and polysynaptic reflexes (see Minassian, Persy, Rattay, Pinter, Kern, and Dimitrijevic, supra), we suggest that noninvasive tESCS can be an effective way to neuromodulate the SN.

Experiment

We examined six adult male subjects (students and staff of the Velikie Luki State Academy of Physical Education and Sports). They had given their informed written consent to participate in the experiment. The experiment was approved by the Ethics Committee of the academy and met the requirements of the Helsinki Declaration.

The subjects lay on a couch on their left side, with their feet placed on separate boards that were attached to a hook in the ceiling of the experimental room with ropes, like swings. The right (upper) leg was supported directly in the region of the shank. The left (lower) leg was placed in a rotating frame attached to a horizontal board. Under these conditions, the subjects could move their legs through maximum amplitude: According to the instructions, the subjects lay quietly and neither counteracted nor facilitated the movements caused by electrical stimulation of the spinal cord.

The tESCS was performed using a KULON stimulator (St. Petersburg State University of Aerospace Instrumentation, St. Petersburg, Russia). The stimulation was administered using a 2.5 cm round electrode (Lead-Lok, Sandpoint, United States) placed midline on the skin between the spinous processes of T11 and T12 as a cathode and two 5.0×10.2 cm rectangular plates made of conductive plastic (Ambu, Ballerup, Germany) placed symmetrically on the skin over the iliac crests as anodes. The step-like movements were evoked by a bipolar rectangular stimulus with a duration of 0.5 ms, filled with a carrier frequency of 10 kHz; the intensity of stimulation ranged from 30 to 100 mA. The stimulation frequencies were 1, 5, 10, 20, 30, and 40 Hz; the duration of exposure ranged from 10 to 30 s. During the high-frequency stimulation within each stimulus, tESCS did not cause pain even when the amplitude was increased to 100 mA or more; allowing us to study in detail the dependence of the elicited movements on the amplitude and frequency of the stimulus.

The EMGs of the muscles of both legs (m. rectus femoris, m. biceps femoris, m. tibialis anterior, and m. gastrocnemius) were recorded by means of bipolar surface electrodes. EMG signals were recorded using an ME 6000 16-channel telemetric electroneuromyograph (Mega Win, Finland). Flexion-extension movements in the knee joints were recorded using a goniometer.

The Qualisy video system (Sweden) was used to record the kinematic parameters of leg movements. Light-reflecting markers were attached to the pivot points of the body, which coincided with the rotational axis in the shoulder, hip, knee, and ankle joints. The angular movements in the hip joint were calculated from the location of markers on the lateral epicondyle of the humerus, trochanter, and lateral epicondyle of the femur. The markers that were attached to the trochanter, lateral epicondyle of the femur, and lateral ankle were used to describe the movements in the knee joint. The movements in the ankle joint were estimated by means of the markers located on the lateral epicondyle of the femur, lateral ankle, and the big toe. The reconstruction of movements in one whole step cycle was performed by means of special software. In order to record the movements of the foot tip, the marker was fixed on the big toe of the right foot.

The recording of EMG was synchronized with the recording of stepping kinematical parameters. The average cycle duration and the amplitudes of angular movements were calculated from 10-12 cycles. The duration of a step cycle was calculated on the basis of the interval between two maximum values of angular movements in the hip, knee, and ankle joints. The phase shift between the hip and knee joints was calculated from the interval between the maximum values of angular movements in these joints.

The statistical treatment of the data was performed using a standard software package.

Results

Transcutaneous electrical spinal cord stimulation with a frequency of 5-40 Hz elicited involuntary leg movements in five out of six subjects. The threshold intensity of the stimulus that induced involuntary movements was 50-60 mA and was dependent on the frequency of stimulation. The tESCS at a frequency of 1 Hz caused reflex responses in the leg muscles with a threshold of 70-80 mA (FIG. 1(a)).

Original records of EMG responses in the muscles of the right leg to the tESCS at a frequency of 1 Hz and intensity of 75-100 mA are shown in FIG. 1. Increasing stimulus intensity resulted in an increase in the amplitude of responses. First, the hip muscles (m. rectus femoris and m. biceps femoris) were involved in the motor response; then, the shank muscles (m. tibialis anterior and m. gastrocnemius) were involved (FIG. 1(b)). The response to each stimulus is composed of the early monosynaptic responses (the same is shown in Courtine, Harkema, Dy, Gerasimenko, and Dyhre-Poulsen, supra) with a latency period of about 12-15 ms. Increasing stimulus intensity evoked responses in the biceps femoris muscle (flexor) with a latent period of a few tens of milliseconds, which were, apparently, polysynaptic. Thus, tESCS with a low frequency (1 Hz) elicited reflex responses in the leg muscles that contained mono and polysynaptic components.

Figure 5:
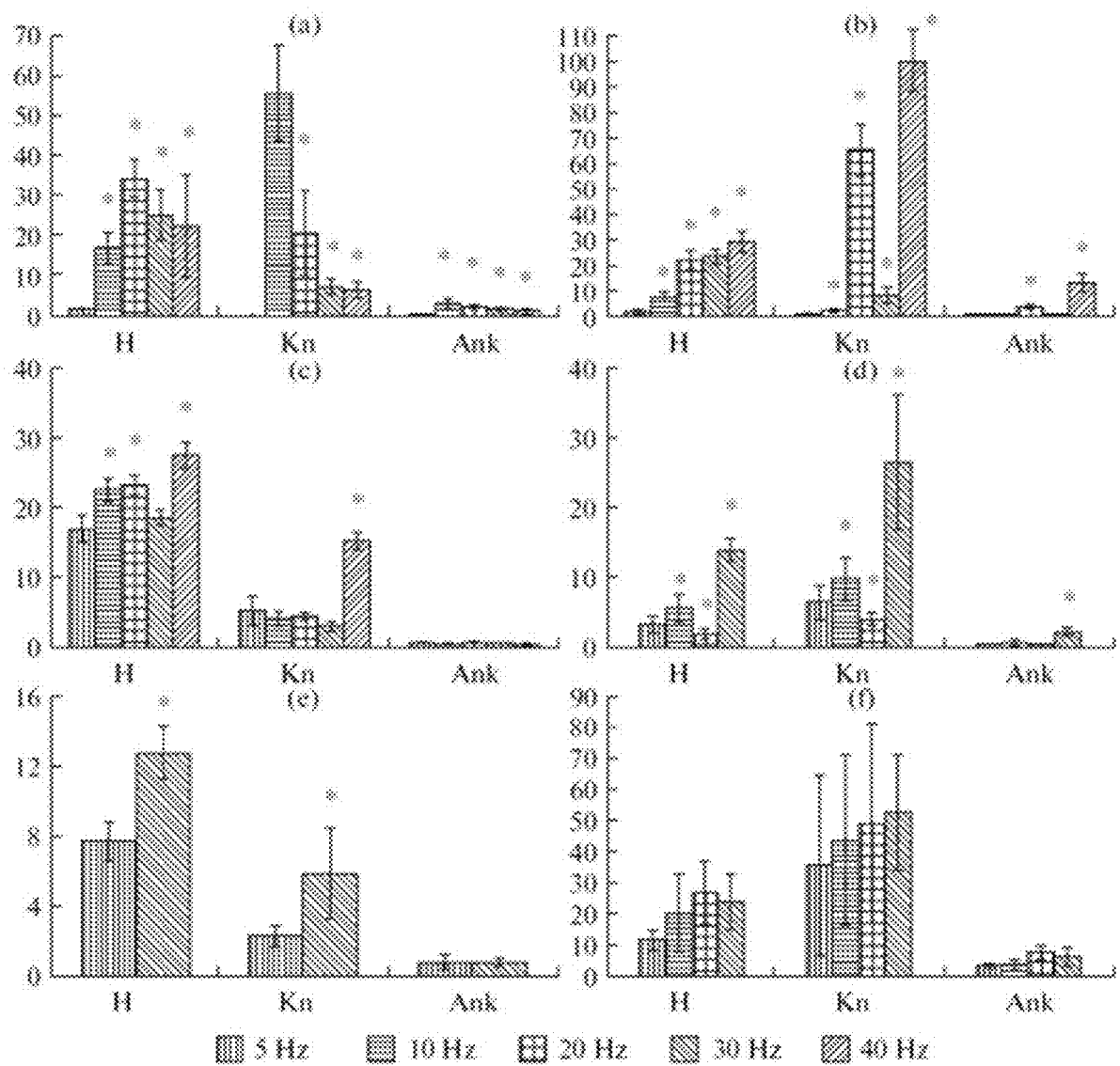
FIG. 5, panels A-F, show the average amplitude of movements in the hip (H), knee (Kn), and ankle (Ank) joints caused by tESCS with a frequency of 5-40 Hz recorded during the first 15 s after the start of stimulation. The ordinate shows angular degrees. (Panels A, B) Subject S, different strategies (Panels A and B); subject R (Panel C); subject K (Panel D); subject B (Panel E); subject G (Panel F). Error bars, standard deviation. Asterisks, significant differences in amplitude recorded during tESCS with a frequency of 5 Hz, $p \leq 0.05$.

Transcutaneous electrical spinal cord stimulation at frequencies in the entire range from 5 to 40 Hz caused step-like movements in five subjects (FIG. 5). There was some variability in the ability of tESCS to evoke step-like movements at different frequencies of stimulation. In two subjects (R. and S.), step-like movements were evoked by tESCS at all the test frequencies in the range 5-40 Hz; in subjects K and G., they were recorded at frequencies of 5, 10, 20, and 30 Hz; and in subject B, they were recorded at frequencies of 5 and 30 Hz. The latent period of the starting of movements did not depend on the frequency of stimulation and was in the range of 0.2-2.5 s. The amplitude of movements in subjects S, G, and R at the beginning of stimulation gradually increased to the maximum, and after its termination it gradually decreased. In subjects K and S, the movements terminated against the background of ongoing tESCS, the duration of the stepping pattern was approximately 10-20 s. In subjects R and S, the movements continued during the whole period of stimulation and ended 2-4 s after its termination.

Pair wise comparison of the mean amplitudes of the movements of the hip, knee, and ankle joints calculated during the first and the last 15 s of stimulation at each of the frequencies used allowed us to determine the probability of the differences in the amplitudes of the induced movements at the beginning and at the end of the stimulation (see Table 1, below). Two rows of probabilities for subject C, calculated on the bases of two experiments show the different direction of the changes in the amplitudes at the beginning and end of stimulation. In the table, the cases when the amplitude of movements at the end of the stimulation was significantly greater than in the beginning are boldfaced; the cases when the amplitude of movements at the end of the stimulation was significantly lower than in the beginning are italicized. According to the data, the subjects were divided into two groups. In the first group (subjects R and S), step-like movements were evoked by the stimulation at the entire range of the frequencies studied (5-40 Hz), and the amplitude of movements, while growing at the beginning of stimulation, decayed after its termination. In the second group (subjects K and S), the movements were evoked with difficulty and with a limited set of frequencies. These differences could be related both to the individual characteristics of the electrical conductivity of the skin and to characteristics of the spinal connections.

Figure 3:
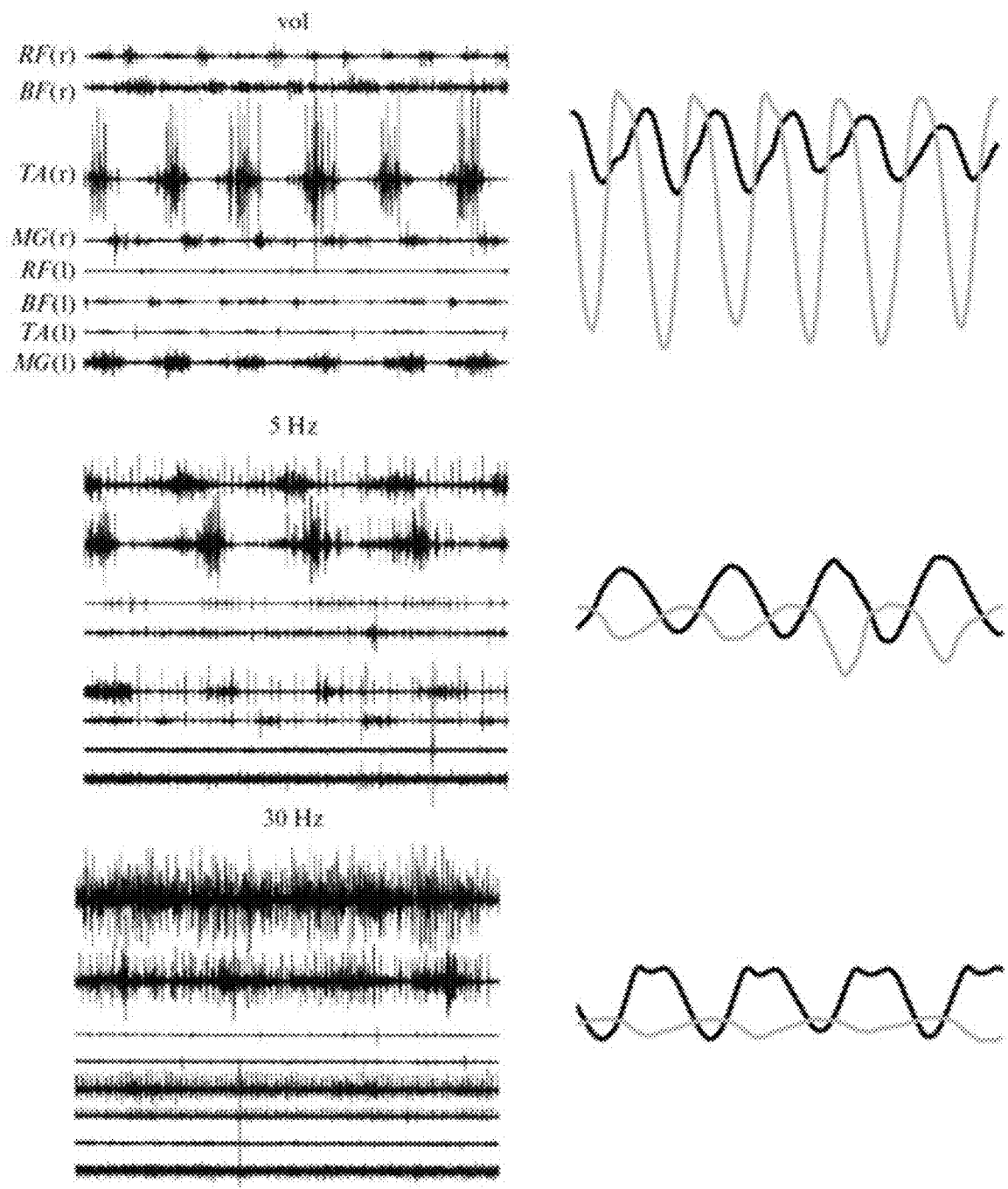
FIG. 3 EMGs (left) and trajectories of reflective markers attached to the right leg; kinematograms (right) recorded during voluntary stepping movements (vol) and movements caused by tESCS with frequencies of 5 and 30 Hz. The duration of records is 10 s. Black and gray lines show movements in the hip and knee joints, respectively. The remaining designations are the same as in FIG. 2A/2B.

The involuntary movements of the legs caused by tESCS fully complied with the characteristics of stepping movements (FIG. 3). Like voluntary stepping movements, the involuntary movements caused by tESCS surely contain the alternating contractions of the similar muscles of the left and right legs and the alternation of antagonist muscle activity in the hip and shin (rectus femoris and biceps femoris, gastrocnemius and tibial muscle of the shin). As clearly seen in the curves reflecting the motion of the hip and knee joints, the movements in these joints, both voluntary and evoked by tESCS, occurred with a phase shift (the motion in the knee ahead of the motion in the hip).

The table below shows the probability of similarity of the mean amplitudes of movements, measured in the first and the last 15 s during tESCS. For subject S., two different cases of stimulation are shown.

TABLE 1

| | | The Frequency of Stimulation | | | | |
|---|---|---|---|---|---|---|
| Subject | Joint | 5 Hz | 10 Hz | 20 Hz | 30 Hz | 40 Hz |
| S. (1) | H | 0.08 | 0.16 | 0.20 | 0.005 | 0.1 |
| | Kn | 0.003 | 0.26 | 0.41 | 0.03 | 0.0003 |
| | Ank | 0.08 | 0.07 | 0.18 | 0.20 | 0.07 |
| S. (2) | H | 0.01 | 0.0001 | 0.004 | 0.82 | 0.92 |
| | Kn | 0.04 | 0.0001 | 0.002 | 0.0004 | 0.12 |
| | Ank | 0.002 | 0.0006 | 0.002 | 0.001 | 0.08 |
| R. | H | 0.07 | 0.05 | 0.14 | 0.27 | *0.007* |
| | Kn | 0.0001 | 0.001 | 0.03 | 0.01 | 0.15 |
| | Ank | 0.02 | 0.008 | 0.003 | 0.47 | 0.68 |
| K. | H | 0.99 | | | | *0.002* |
| | Kn | *0.03* | | | | *0.008* |
| | Ank | 0.21 | | | | *0.001* |

TABLE 1-continued

| | | The Frequency of Stimulation | | | | |
|---|---|---|---|---|---|---|
| Subject | Joint | 5 Hz | 10 Hz | 20 Hz | 30 Hz | 40 Hz |
| B. | H | *0.03* | 0.16 | 0.27 | 0.68 | |
| | Kn | 0.12 | 0.06 | *0.04* | *0.02* | |
| | Ank | *0.05* | 0.99 | 0.15 | *0.001* | |
| G. | H | *0.004* | 0.16 | 0.21 | 0.16 | |
| | Kn | *0.05* | 0.08 | 0.24 | 0.26 | |
| | Ank | *0.005* | *0.05* | 0.29 | *0.009* | |

Notes:
H, hip joint; Kn, knee joint; Ank, ankle joint. The cases where $p \leq 0.05$ are boldfaced and italicized. Other explanations are in the text.

Figure 4:
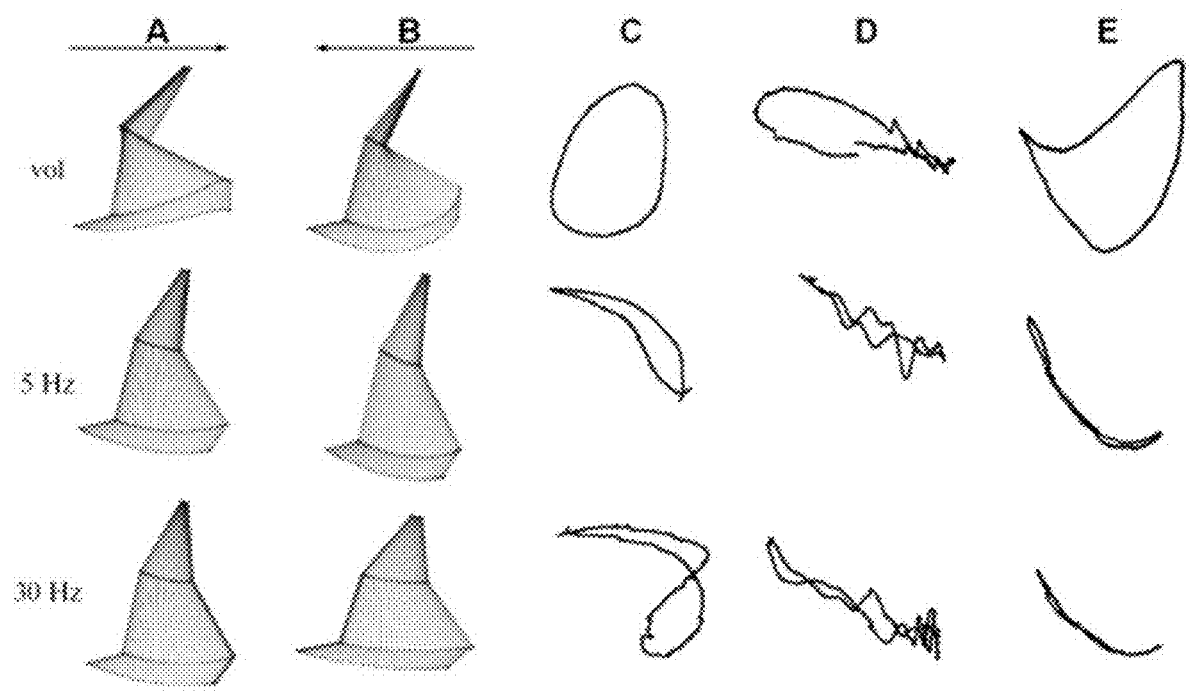
FIG. 4, panels A-E, show interarticular coordination during voluntary stepping movements (vol) and movements caused by tESCS with frequencies of 5 and 30 Hz. Reconstruction of the movements of the right leg during one stepping cycle obtained by processing the cinematograms of the (Panel A) forward and (Panel B) backward movements of legs, respectively; the coordination of movements in the (Panel C) hip and knee joints, (Panel D) knee and ankle joints; and (Panel E) the trajectory of a big toe.

Stepping cycles in three joints of the right leg during voluntary stepping movements (FIG. 4) and movements elicited by tESCS reconstructed on the basis of the kinematic analyses. The swing (A) and stance (B) phase and the hip-knee (C) and knee-ankle (D) angles and the X,Y trajectory of the toe (E) during a step are shown for voluntary movement and during tESCS at 5 and 30 Hz. In step-like movements elicited by tESCS, as in voluntary stepping movements, the phase of carrying the leg forward and the phase of support during the backward leg movements were distinct (FIG. 4). During voluntary movements, the patterns of the knee and ankle joints are more complex than during the elicited movements. The coordination between the joints during the evoked movements is very different from that observed during voluntary movements (FIG. 4). The same is true for the movements of the distal region of the leg, resulting from the interaction of movements in all three joints, and recorded using a marker attached to the big toe. The trajectory of the terminal point in voluntary movements looked like an ellipse. The trajectory of the terminal point in the movements elicited by tESCS may be considered a confluent ellipse, with the leg moving forward and backward without significant vertical movements.

The frequency of step-like movements did not depend on the frequency of stimulation. The average periods of step-like movements in subjects R, S, K, B, and G were 2.72±0.14, 2.39±0.55, 2.42±0.15, 3.22±0.85, and 1.9±0.09 s, respectively.

As mentioned above, the pair wise comparison of the mean amplitudes of the movements in the hip, knee, and ankle joints calculated in the first and the last 15 s of stimulation in different subjects, showed that, regardless of the stimulation frequency, the amplitude of movements may either increase or decrease significantly. At the beginning of stimulation, there was a tendency for the amplitude of movements to increase with increasing frequency of stimulation in all subjects for all joints (FIG. 5). However, at the end of stimulation, the amplitude of movements was independent of the stimulation frequency. In all joints, minimum movements were observed at a stimulation frequency of 5 Hz (FIGS. 5 (b) and (d)). As an exception, only in one case, when subject S. was stimulated, the amplitude of movements in the hip joint increased with increasing stimulation frequency and the amplitude of movements in the knee and ankle joints decreased with increasing frequency [FIG. 5; table 1, subject S. (1)]. The trajectory of movement of the big toe of this subject, reflecting the amplitude of the whole leg's movement, is shown in FIG. 5(a). In this case, the amplitude of movement of the tip of the foot at stimulation frequencies of 10, 20, 30, and 40 Hz was, respectively, 15.0, 19.9, 15.3, and 16.4 times greater than at 5 Hz. In the case shown in FIG. 5(b), it was, respectively, 3.5, 9.4, 11.3, and 80.7 times greater than at 5 Hz. Thus, in this subject, with increasing frequency of stimulation, the amplitude of leg movements did not decrease in any of the cases; it was minimal at a frequency of 5 Hz.

Note that, in the cases shown in FIGS. 5 (b) and (d), an increase in frequency resulted in a significant increase in the amplitude of movements in the ankle joint. The possibility to control the movements in the ankle joint via the frequency of stimulation was an advantage of tECS, unlike the ankle joint which was not modulated in vibration-induced step-like movements. See Gorodnichev, Machueva, Pivovarova, Semenov, Ivanov, Savokhin, Edgerton, and Gerasimenko, supra.

DISCUSSION

Recently, it was shown that transcutaneous electrical stimulation of the lumbar enlargement may facilitate passive walking movements on a moving treadmill and strengthen the patterns of EMG activity in leg muscles in patients with complete or partial spinal cord lesions. See Minassian, Persy, Rattay, Pinter, Kern, and Dimitrijevic, supra. However, involuntary step-like movements were never successfully evoked by means of transcutaneous stimulation in this category of patients before. The transcutaneous electrical stimulation applied to the rostral segments of the lumbar enlargement (in the region of the T11-T12 vertebrae) elicited involuntary step-like movements in healthy subjects with their legs suspended in a gravity-neutral position. This phenomenon was observed in five out of the six subjects studied. tESCS did not cause discomfort and was easily tolerated by subjects when biphasic stimuli filled with a carrier frequency of 10 kHz which suppressed the sensitivity of pain receptors were used.

The Proof of the Reflex Nature of the Responses Evoked by tESCS

It was found that a single transcutaneous electrical stimulation in the region of the T11-T12 vertebrae causes responses in leg muscles with a latency period corresponding to monosynaptic reflexes. See Courtine, Harkema, Dy, Gerasimenko, and Dyhre-Poulsen, supra. It is assumed that these responses are due to the activation of large-diameter dorsal root afferents. See Minassian, Persy, Rattay, Pinter, Kern, and Dimitrijevic, supra; Dy, C. J., Gerasimenko, Y P., Edgerton, V R., DyhrePoulsen P., Courtine G., Harkema S., Phase-Dependent Modulation of Percutaneously Elicited Multisegmental Muscle Responses after Spinal Cord Injury, J Neurophysiol., 2010, vol. 103, p. 2808; de Noordhout, A., Rothwell, J. e., Thompson, P. D., Day, B. L., and Marsden, e. D., Percutaneous Electrical Stimulation of Lumbosacral Roots in Man, J Neurol. Neurosurg. Psychiatry, 1988, vol. 51, p. 174; Troni, W., Bianco, e., Moja, M. C., and Dotta, M., Improved Methodology for Lumbosacral Nerve Root Stimulation, Afuscle Nerve, 1996, vol. 19, no. Iss. 5, p. 595; Dyhre-Poulsen, P., Dy, Courtine, G., Harkema, S., and Gerasimenko, Y U. P., Modulation of Multi segmental Monosynaptic Reflexes Recorded from Leg Muscles During Walking and Running in Human Subjects, Gait Posture, 2005, vol. 21, p. 66. The monosynaptic nature of these responses is confirmed by the fact that vibration of muscle tendons or paired stimulation suppresses the responses. We have previously shown that the responses to the second stimulus were suppressed in rats during epidural stimulation (see Gerasimenko, Lavrov, Courtine, Ronaldo, Ichiyama, Dy, Zhong, Roy, and Edgerton, supra) and in healthy humans (see Courtine, Harkema, Dy, Gerasimenko, and Dyhre-Poulsen, supra; Dy, Gerasimenko, Edgerton, Dyhre-Poulsen, Courtine, Harkema, supra) during paired tESCS with a delay between the stimuli of 50 ms. This refractory period excludes the possibility of direct activation of the motor neurons in the ventral horn or ventral root activation. See Struijk, 1.1., Holsheimer, 1., and Boom, H. B. K., Excitation of Dorsal Root Fibers in Spinal Cord Stimulation: A Theoretical Study, IEEE Trans. Biorned. Eng., 1993, vol. 40, no. 7, p. 632. The monosynaptic nature of the responses was also shown during vibration tests. It is well known that vibration suppresses monosynaptic reflex pathways in homologous muscles. See Mao, e.e., Ashby, P., Wang, M., and McCrea, D., Synaptic Connections from Large Muscle Afferents to the Motoneurons of Various Leg Muscles in Man, Exp. Brain Res., 1984, vol. 56, p. 341. The suppression of responses caused by tESCS in shin muscles during the vibration of the Achilles tendon directly shows the monosynaptic nature of these responses. The similarity of modulations of the classical monosynaptic H-reflex and reflex responses caused by tESCS during walking in healthy subjects (see Courtine, Harkema, Dy, Gerasimenko, and Dyhre-Poulsen, supra) and in patients with spinal cord injuries (see Dy, Gerasimenko, Edgerton, Dyhre-Poulsen, Courtine, Harkema, supra) also supports the monosynaptic nature of the responses to transcutaneous stimulation. In both cases, the amplitude of modulation of the reflexes was proportional and phase-dependent on the activation level of each muscle. All of the above data indicate the identity of the H-reflex and reflex responses induced by tESCS.

In the flexor muscles affected by tESCS, polysynaptic reflexes were sometimes recorded in addition to the monosynaptic component (FIG. 1). Earlier, we recorded polysynaptic reflexes in the flexor the intact and spinal animals during the single epidural stimulation. See Gerasimenko, Lavrov, Courtine, Ronaldo, Ichiyama, Dy, Zhong, Roy, and Edgerton, supra; Lavrov, 1., Gerasimenko, Y U. P., Ichiyama, R., Courtine G., Zhong H., Roy R., and Edgerton R. V, Plasticity of Spinal Cord Reflexes after a Complete Transection in Adult Rats: Relationship to Stepping Ability, J Neurophysiol., 2006, vol. 96, no. 4, p. 1699. All the above data suggest that tESCS can activate mono and polysynaptic neuronal networks.

The Characteristics of Transcutaneous Stimulation Eliciting Step-Like Movements

The previous experiments showed that the rostral segments of the lumbar spinal cord may play the role of triggers in initiating locomotor movements. See Deliagina, T. G., Orlovsky, G. N., and Pavlova, G. A., The Capacity for Generation of Rhythmic Oscillations Is Distributed in the Lumbosacral Spinal Cord of the Cat, Exp. Brain Res., 1983, vol. 53, p. 81. In spinal patients (see Dimitrijevic, M. R, Gerasimenko, Yu., and Pinter, M. M., Evidence for a Spinal Central Pattern Generator in Humans, Ann. N. Y. Acad. Sci., 1998, vol. 860, p. 360) and in spinal rats (Ichiyama, R. M., Gerasimenko, Y U. P., Zhong, H., Roy, R. R., and Edgerton VR., Hindlimb Stepping Movements in Complete Spinal Rats Induced by Epidural Spinal Cord Stimulation, New•osci. Lett., 2005, vol. 383, p. 339), step-like patterns of EMG activity were evoked by epidural stimulation of the L2 segment. In our experiments, we used transcutaneous electrical stimulation in the region of T11-T12 vertebrae, which corresponds to the cutaneous projection of the L2-L3 segments of the spinal cord. It was previously shown that the electromagnetic stimulation of this region in healthy subjects with their legs supported externally can initiate walking movements. See Gerasimenko, Gorodnichev, Machueva, Pivovarova, Semenov, Savochin, Roy, and Edgerton, supra; Gorodnichev, Machueva, Pivovarova, Semenov, Ivanov, Savokhin, Edgerton, and Gerasimenko, supra. These data are consistent with the current concept on the structural and functional organization of the SN with distributed pacemaking and pattern-generating systems (see McCrea, D. A. and Rybak, L A., Organization of Mammalian Locomotor Rhythm and Pattern Generation, *Brain Res. Rev.,* 2008, vol. 57, no. 1, p. 134), in which the rostral lumbar segments of the spinal cord play the role of a trigger of the locomotor function.

The frequency of stimulation is an important characteristic of the motor output. It was shown that step-like movements are evoked by stimulation frequencies in the range of 5-40 Hz. The amplitude of step-like movements induced by high-frequency stimulation (30-40 Hz) was usually higher than that of the movements induced by low frequency stimulation (5 Hz), although the duration of the stepping cycle varied slightly. The fact that a wide range of frequencies can effectively induce step-like movements is probably due to the functional state of the intact spinal cord and its pathways. For example, in spinal patients, the effective frequency range for the initiation of step-like movements using epidural stimulation was 30-40 Hz (according to Dimitrijevic, Gerasimenko, and Pinter, supra); in decerebrated cats, the frequency of 5 Hz was the most effective to elicit locomotion (according to our data) (see Gerasimenko, Roy, and Edgerton, supra).

The intensity of transcutaneous electrical stimulation (50-80 mA) that causes step-like movements is approximately 10 times higher than the intensity of the epidural stimulation initiating walking movements in spinal patients. See Dimitrijevic, Gerasimenko, and Pinter, supra. If we assume that the dorsal roots are the main target for both types of stimulation, we should agree that the current should be strong to activate them by transcutaneous electrical stimulation. Thus, we conclude that the location, frequency, and intensity of stimulation are the factors that determine the activation of the SN by tESCS.

The Origin of the Stepping Rhythm Evoked by tESCS

Figure 2A:
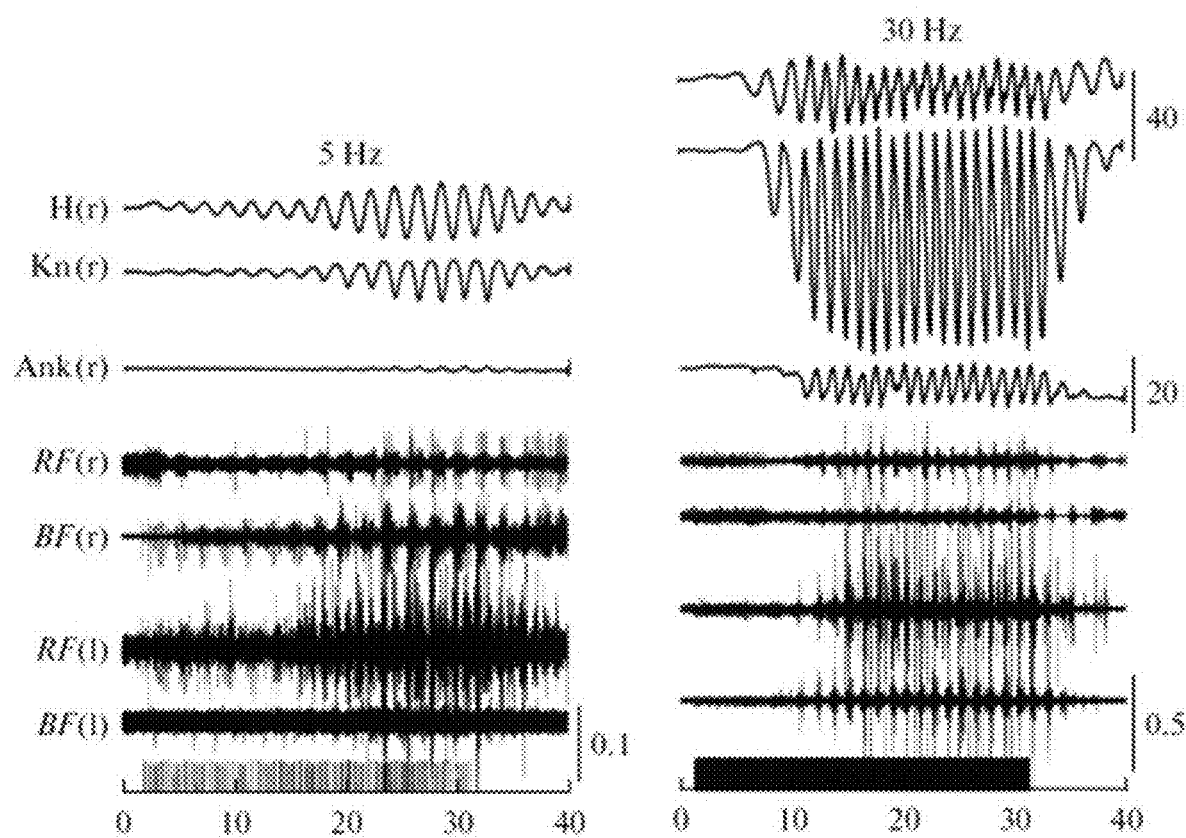
FIGS. 2A and 2B show electrical activity of the leg muscles and movements in the leg joints evoked by tESCS with frequencies of 5 and 30 Hz.
Figure 2B:
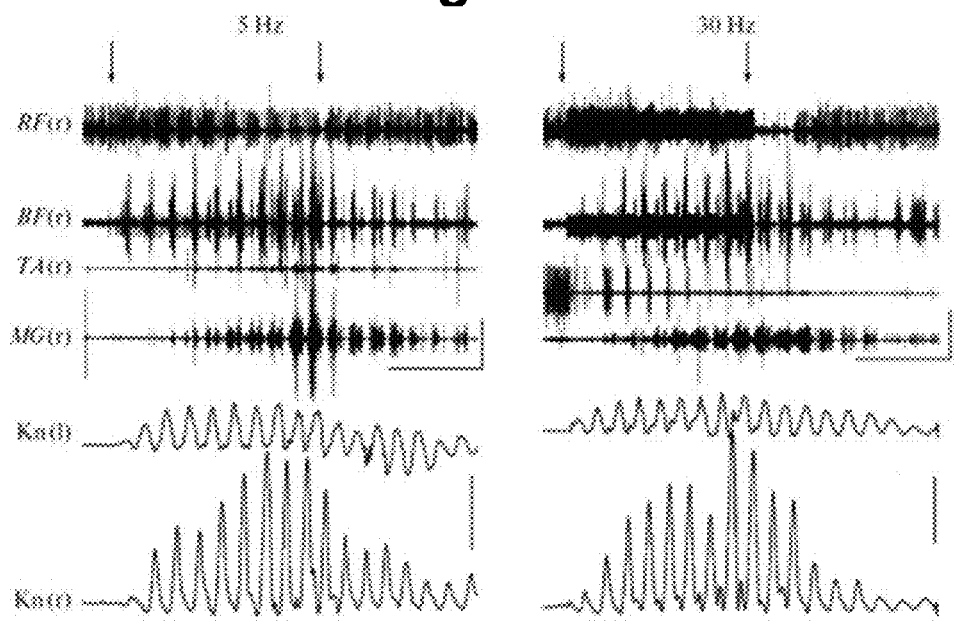

In most subjects, the involuntary step-like movements in the hip and knee joints were initiated by tESCS with a delay of 2-3 s after the start of stimulation. Typically, the amplitude of movements in the hip and knee joints increased smoothly and gradually with the subsequent involvement of the ankle joint (FIG. 2B). A similar character of the initiation of involuntary step-like movements with gradual involvement of different motor pools of the leg muscles was also observed during the vibration of muscles (see Gurfinkel', Levik, Kazennikov, and Selionov, supra; Selionov, Ivanenko, Solopova, and Gurfinkel', supra; Gorodnichev, Machueva, Pivovarova, Semenov, Ivanov, Savokhin, Edgerton, and Gerasimenko, supra) and the epidural spinal cord stimulation. See Dimitrijevic, Gerasimenko, and Pinter, supra; Minassian, Persy, Rattay, Pinter, Kern, and Dimitrijevic, supra. This suggests that transcutaneous electrical stimulation, as well as the epidural stimulation, affects the SN through the activation of the dorsal root afferents entering the spinal cord. In addition to the dorsal roots and dorsal columns, the direct stimulation of the spinal cord may also activate the pyramidal and reticulospinal tracts, ventral roots, motor neurons, dorsal horn, and sympathetic tracts. See Barolat, G., Current Status of Epidural Spinal Cord Stimulation, *Neurosurg. Quart.,* 1995, vol. 5, no. 2, p. 98; Barolat, G., Epidural Spinal Cord Stimulation: Anatomical and Electrical Properties of the Intraspinal Structures Relevant To Spinal Cord Stimulation and Clinical Correlations, *Neuromodul. Techn. Neur. Intelf-,* 1998, vol. 1, no. 2, p. 63. During the tESCS, the electric current spreads perpendicular to the spinal column with a high density under the paravertebral electrode. See Troni, Bianco, Moja, and Dotta, supra. This stimulation apparently activates the dorsal roots immersed in the cerebrospinal fluid, but not the spinal cord neurons, which have a much lower conductivity. See Holsheimer, J., Computer Modeling of Spinal Cord Stimulation and Its Contribution to Therapeutic Efficacy, *Spinal Cord,* 1998, vol. 36, no. 8, p. 531. We assume that tESCS consequently involves in activity the afferents of groups Ia and Ib with the largest diameter and, thus, the lowest threshold, then the afferents of the group II, and the spinal interneurons mediating polysynaptic reflexes. The presence of polysynaptic components in the evoked potentials in the flexor muscles (FIG. 1) confirms that they participate in the SPG. Thus, we can say that tESCS activates different spinal neuronal systems; however, the dorsal roots with their mono and polysynaptic projections to the motor nuclei are the main ones among them. The contribution of mono and polysynaptic components in the formation of the stepping rhythm caused by tESCS is not known.

In our studies, single pulse stimulation resulted in monosynaptic reflexes in the majority of the leg muscles investigated. However, the electromyographic trains evoked by continuous tESCS that induced involuntary step-like movements were not formed by the amplitude modulation of monosynaptic reflexes, as it was in spinal rats and during the spinal epidural stimulation of patients. See Gerasimenko, Roy, and Edgerton, supra. Our data showed that the activity within electromyographic trains was not stimulus-dependent; i.e., EMG trains did not consist of separate reflex responses. Similar stimulus-independent EMG trains were observed during involuntary movements caused by spinal cord electromagnetic stimulation. See Gerasimenko, Gorodnichev, Machueva, Pivovarova, Semenov, Savochin, Roy, and Edgerton, supra; Gorodnichev, Machueva, Pivovarova, Semenov, Ivanov, Savokhin, Edgerton, and Gerasimenko, supra. In contrast, the step-like movements evoked by the epidural spinal stimulation in rats and spinal patients were stimulus-dependent. See Gerasimenko, Roy, and Edgerton, supra. In the extensor muscles, the EMG trains consisted mainly of monosynaptic reflexes; in the flexor muscles, polysynaptic reflexes dominated in the EMG trains. See Gerasimenko, Y. P., Ichiyama, R. M., Lavrov, L A., Courtine, G. Cai, L., Zhong, H., Roy, R. R., and Edgerton, V. R., Epidural Spinal Cord Stimulation Plus Quipazine Administration Enable Stepping in Complete Spinal Adult Rats, *J Neurophysiol.,* 2007, vol. 98, p. 2525; Minassian, K., Jilge, B., Rattay, F., Pinter, M. M., Binder, H., Gerstenbrand, F., and Dimitrijevic, M. R., Stepping-Like Movements in Humans with Complete Spinal Cord Injury Induced by Epidural Stimulation of the Lumbar Cord: Electromyographic Study of Compound Muscle Action Potentials, *Spinal Cord* 2004, vol. 42, p. 401. It is not clear why single cutaneous and, respectively, single epidural spinal cord stimulation causes the same monosynaptic reflexes in healthy subjects and spinal patients; however, continuous stimulation elicits their step-like movements through different mechanisms. We assume that, in healthy subjects, tESCS increases the excitability of the neuronal locomotor network, being a trigger for its activation, in the same way as in the case of vibration-induced step-like movements. See Selionov, Ivanenko, Solopova, and Gurfinkel', supra. However, we need additional studies to understand in detail how the tESCS elicits involuntary step-like movements.

CONCLUSIONS

In this study, a new noninvasive access to locomotor spinal neural networks in humans by means of tESCS has been described. A special design of the stimulator, which generated bipolar pulses filled with high-frequency carrier, allowed us to stimulate the spinal cord relatively painlessly and elicit involuntary step-like movements. The fundamental importance of our study consists in the new data in favor of the existence of SPGs in humans and the evidence of the possibility to control the SPGs using noninvasive effects on the structures of the spinal cord. This opens up good prospects for widespread use of transcutaneous techniques in electrical spinal cord stimulation to study the mechanisms underlying the regulation of the locomotor behavior in healthy subjects and for the rehabilitation and motor recovery of patients after spinal cord injuries.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of enabling, in a mammal that has a brain or spinal cord injury, voluntary control over one or more functions selected from a group consisting of postural and/or locomotor activity, voluntary movement of leg position, and/or voluntary voiding of the bladder, said method comprising administering non-invasive transcutaneous electrical stimulation (tESCS) over the brainstem or spinal cord of said mammal at a frequency and intensity that stimulates the spinal cord circuitry and enables said one or more functions, where said transcutaneous electrical stimulation does not electrically induce said function, but enables the spinal circuitry to receive proprioceptive information and to induce stepping, standing, grasping, and/or reaching, or voiding of the bladder.

2. The method of claim 1, wherein said mammal is a human.

3. The method of claim 2, wherein said transcutaneous electrical spinal cord stimulation is applied over at least one of a lumbosacral portion of the spinal cord, a thoracic portion of the spinal cord, a cervical portion of the spinal cord and/or the brainstem.

4. The method of claim 1, wherein:
said transcutaneous stimulation is applied at an intensity ranging from about 10 mA to about 150 ma; and/or
said transcutaneous stimulation is applied at a frequency ranging from about 3 Hz to about 100 Hz.

5. The method of claim 1, wherein said mammal has a spinal cord injury that is clinically classified as motor complete.

6. The method of claim 1, wherein said mammal has a spinal cord injury that is clinically classified as motor incomplete.

7. The method of claim 1, wherein said mammal has an ischemic brain injury or a neurodegenerative brain injury.

8. The method of claim 1, wherein said locomotor activity comprises:
a walking motor pattern; and/or
standing, stepping, speech, swallowing or breathing; and/or
sitting down or laying down.

9. The method of claim 1, wherein the stimulation is under control of the subject.

10. The method of claim 1, wherein said method further comprises physical training of said mammal.

11. The method of claim 10, wherein said physical training comprises inducing a load bearing positional change in said mammal.

12. The method of claim 11, wherein the load bearing positional change in said subject comprises standing, and/or stepping.

13. The method of claim 10, wherein said physical training comprises robotically guided training.

14. The method of claim 1, wherein said method further comprises administration of one or more neuropharmaceuticals.

15. The method of claim 1, wherein said stimulation enables the spinal circuitry to receive proprioceptive information from the arms and/or legs and to induce stepping, standing, grasping, or reaching.

* * * * *